(12) United States Patent
Coe et al.

(10) Patent No.: US 7,500,941 B2
(45) Date of Patent: Mar. 10, 2009

(54) FOLDING SYSTEM AND PROCESS FOR A CONTINUOUS MOVING WEB OPERATION

(75) Inventors: Richard George Coe, Cincinnati, OH (US); Claudio Antonio Matos, Belleville (CA); Kazuya Ogawa, Akashi (JP); Michael Joseph Page, Springfield Township, OH (US); Richard William Hamm, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 82 days.

(21) Appl. No.: 11/516,356

(22) Filed: Sep. 6, 2006

(65) Prior Publication Data

US 2007/0107918 A1 May 17, 2007

Related U.S. Application Data

(60) Provisional application No. 60/715,413, filed on Sep. 9, 2005.

(51) Int. Cl.
*B31F 1/08* (2006.01)
(52) U.S. Cl. ............... 493/438; 493/436; 493/446; 493/447; 493/455; 493/456; 493/960
(58) Field of Classification Search ............. 493/379, 493/344, 352, 356–358, 365, 370, 418, 436, 493/438–439, 446–447, 450, 455, 456, 960
See application file for complete search history.

(56) References Cited

U.S. PATENT DOCUMENTS

| | | | | |
|---|---|---|---|---|
| 4,558,581 | A | * | 12/1985 | Goulstone et al. ............. 72/176 |
| 5,300,007 | A | * | 4/1994 | Kober ......................... 493/23 |
| 5,435,802 | A | * | 7/1995 | Kober ......................... 493/23 |
| 5,556,360 | A | * | 9/1996 | Kober et al. .................. 493/23 |
| 5,800,329 | A | * | 9/1998 | Fager et al. .................. 493/417 |
| 5,807,228 | A | | 9/1998 | Smithe et al. |
| 5,868,727 | A | | 2/1999 | Barr et al. |
| 5,873,809 | A | * | 2/1999 | Kempster et al. ........... 493/464 |

(Continued)

FOREIGN PATENT DOCUMENTS

EP    1 438 945 B1    11/2006

OTHER PUBLICATIONS

PCT International Search Report dated Feb. 20, 2007.

*Primary Examiner*—Christopher Harmon
(74) *Attorney, Agent, or Firm*—Gary J. Foose; Roddy M. Bullock

(57) ABSTRACT

A folding system is provided for folding at least one wing extending from a central chassis of each of a plurality of absorbent articles formed from a continuous moving web moving in a longitudinal direction. The folding system has a wing-folding conveyor and at least one elongated, folding plow, which has an entrance end, an exit end and an inner edge that define a twist axis. The folding plow has a contoured surface having a configuration defined by a twist angle that increases along the twist axis from zero degrees near the entrance end to 180 degrees near the exit end. The wing-folding conveyor moves the central chassis along the inner edge of the folding plow and the wing slides against the contoured surface from the entrance end to the exit end, such that the wing folds around the central chassis near the inner edge.

17 Claims, 20 Drawing Sheets

U.S. PATENT DOCUMENTS 6,210,309 B1    4/2001  Smithe et al.
6,557,466 B2 *  5/2003  Codde et al. ................ 101/216
6,699,166 B2 *  3/2004  Walter et al. ................ 493/446
6,821,370 B2 * 11/2004  Tomsovic et al. ........... 156/200
6,971,981 B2 * 12/2005  Dobslaw et al. ............. 493/346

* cited by examiner

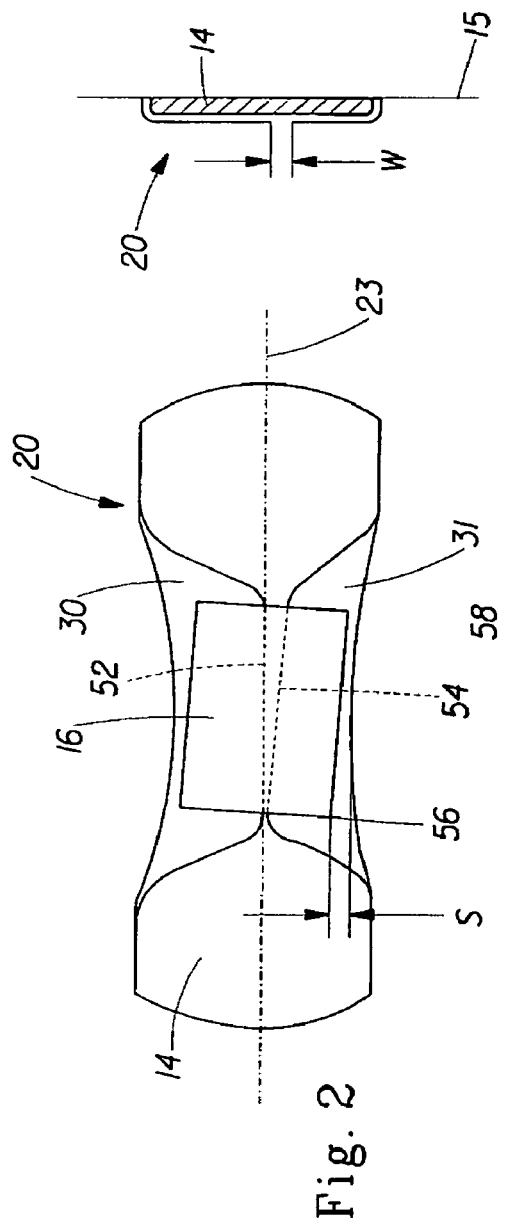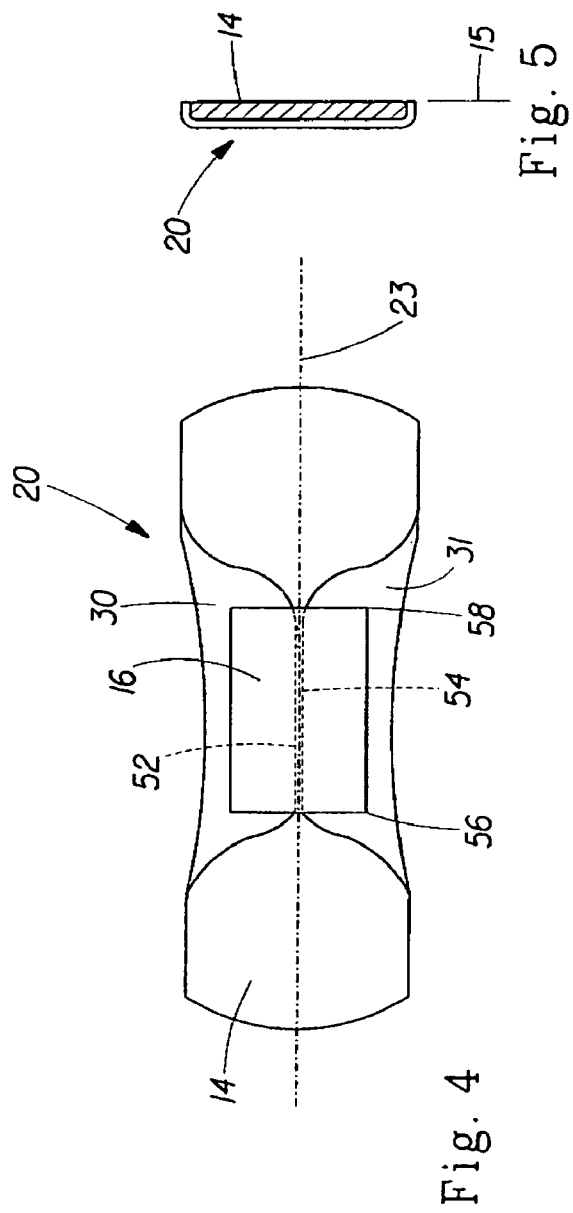

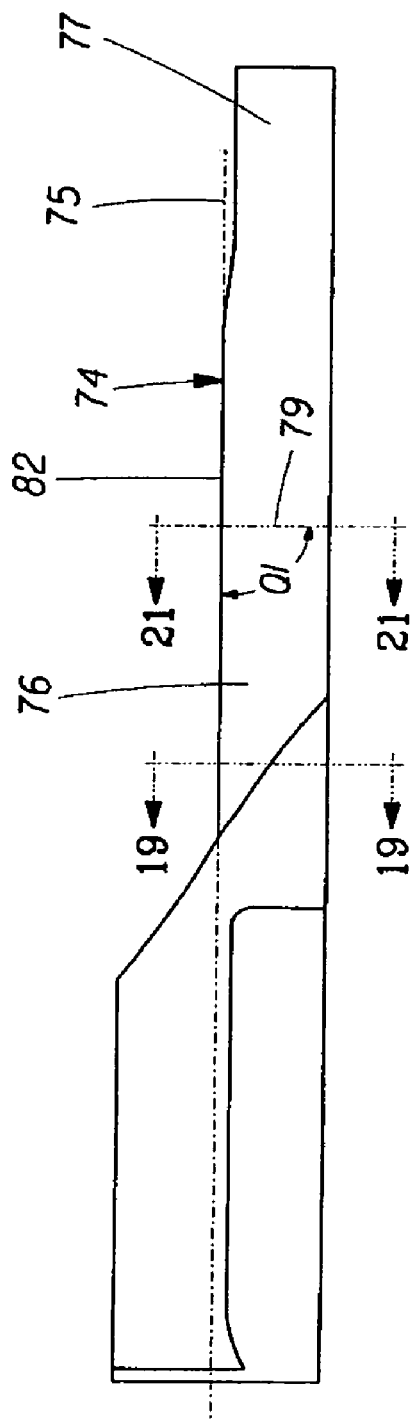
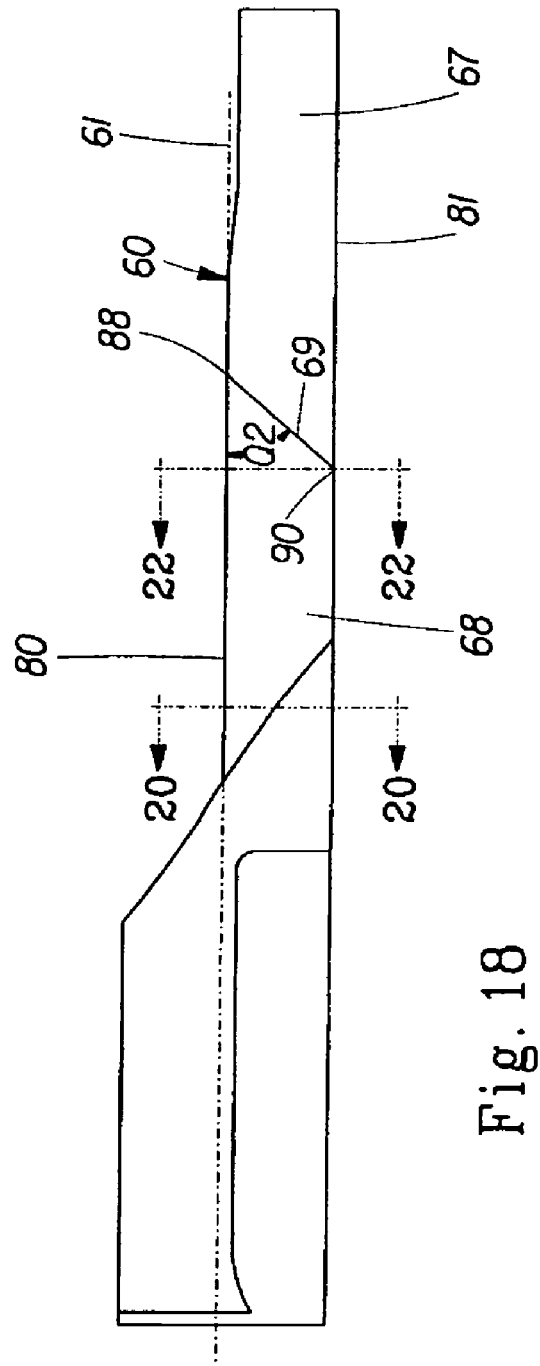
Fig. 17
Fig. 18

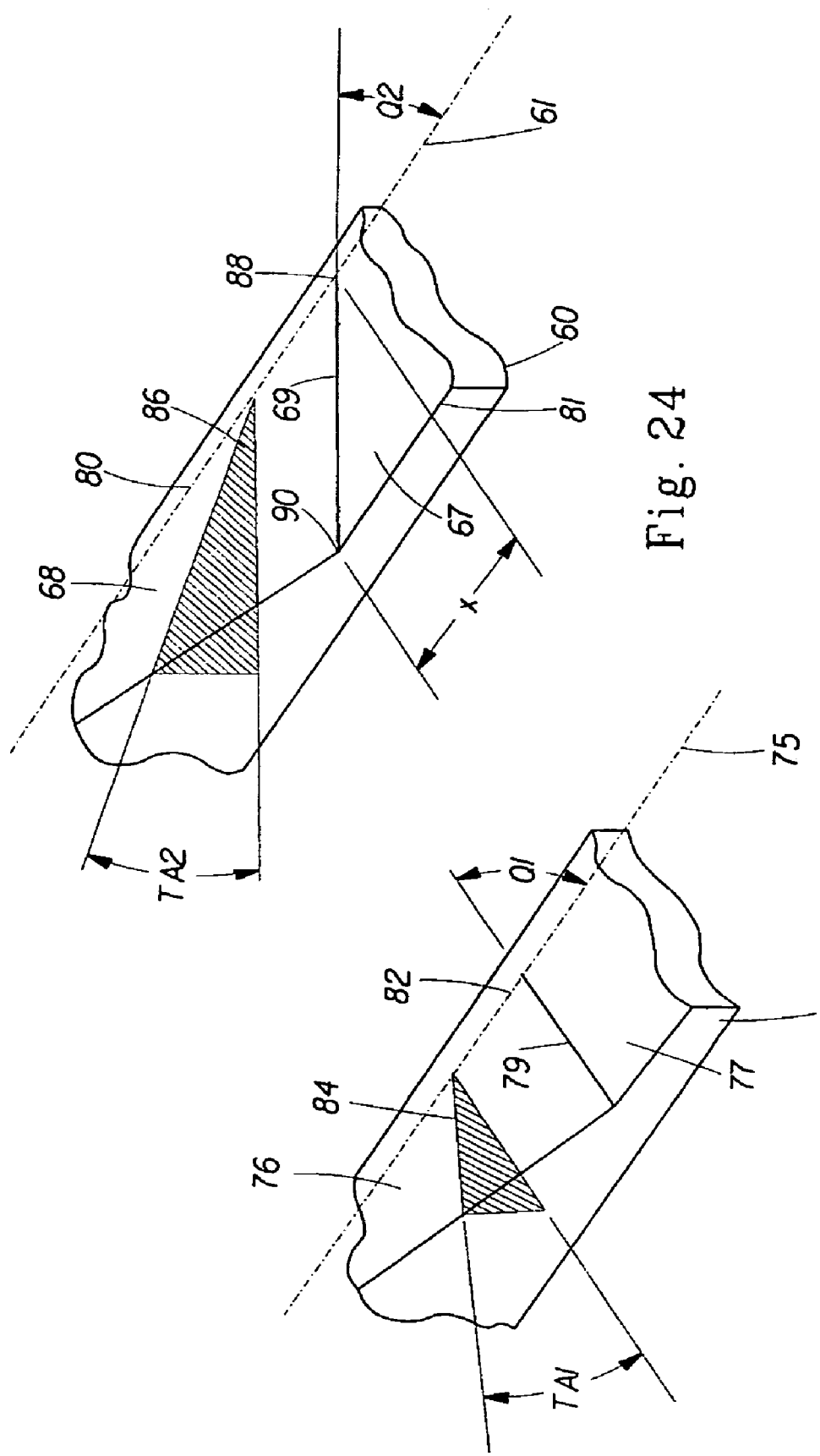

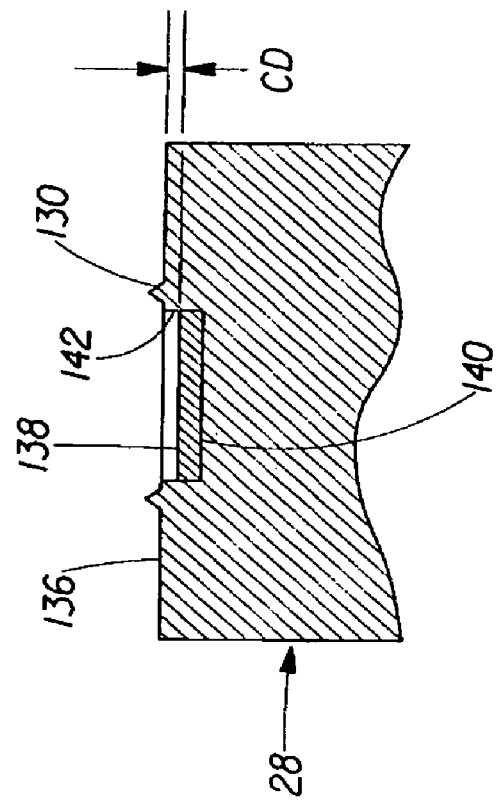
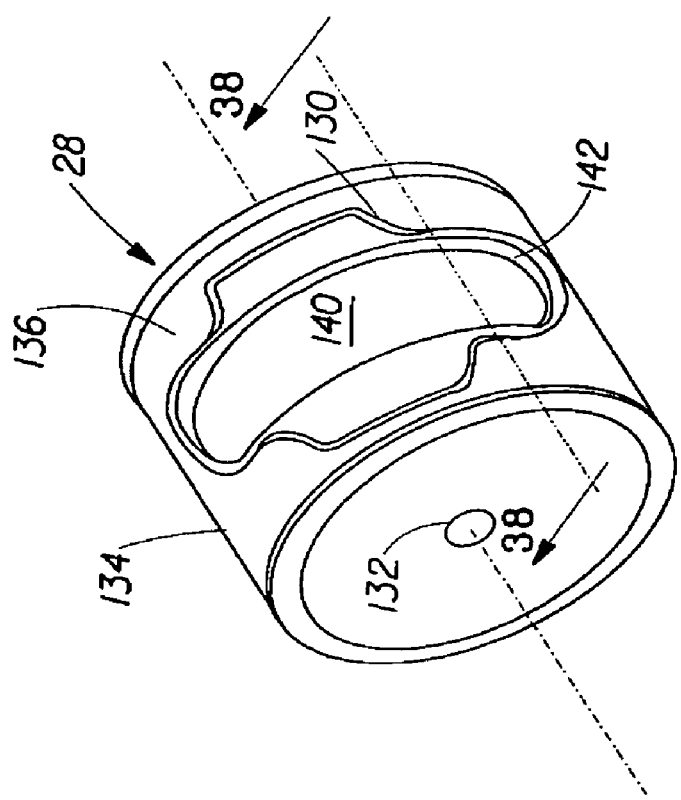
Fig. 37
Fig. 38

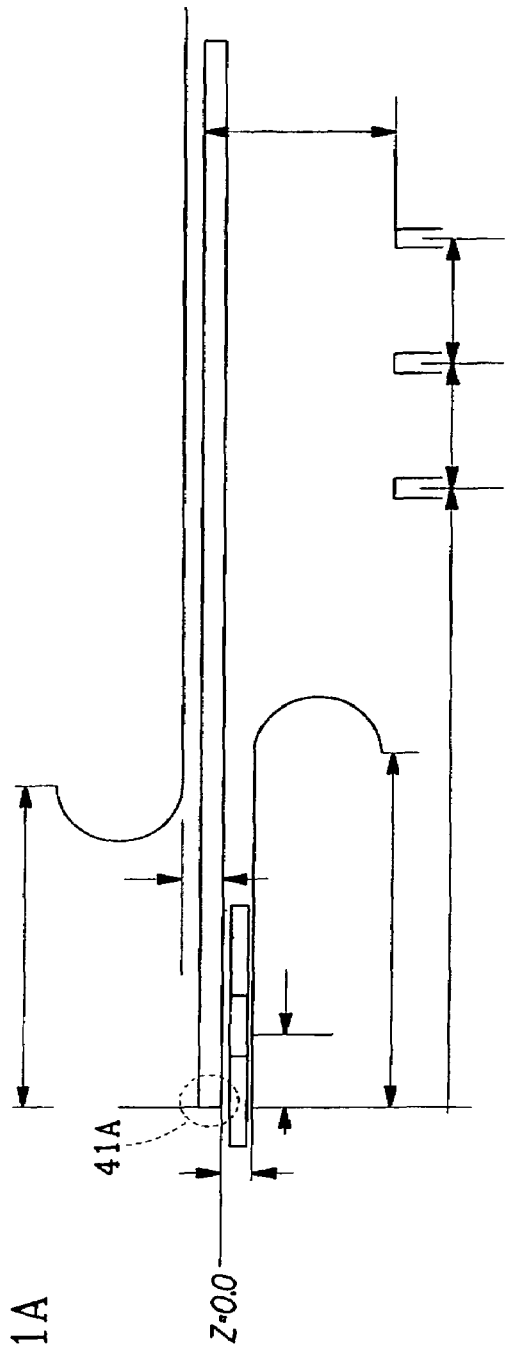
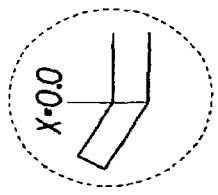
Fig. 41A
Fig. 41
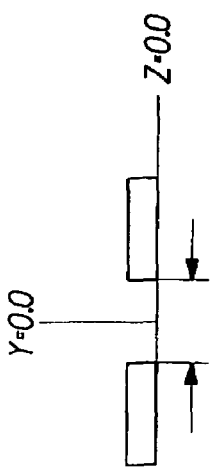
Fig. 41B

FOLDING SYSTEM AND PROCESS FOR A CONTINUOUS MOVING WEB OPERATION

CROSS REFERENCE TO RELATED APPLIATION

This application claims the benefit of U.S. Provisional Application No. 60/715,413, filed Sep. 9, 2005.

FIELD OF THE INVENTION

The present application relates to systems and processes for folding articles formed and cut from a continuous moving web of material in a manufacturing operation. More particularly, the present application relates to systems and processes for folding disposable, absorbent articles formed and cut from a continuous moving web of material in a manufacturing operation.

BACKGROUND OF THE INVENTION

There are many well-known varieties of feminine hygiene products, baby and adult diapers, tissues, wipes and other implements configured for the absorption of human body fluids. Some of these products, such as sanitary napkins and panty liners, have a pair of wings or flaps that extend laterally from the longitudinal side edges of an absorbent, central portion and are intended to be folded around the edges of the wearer's undergarment during use.

In the manufacturing process of these absorbent articles, a continuous web of layered materials typically is driven through a high-speed machine to form several hundred articles per minute. The web may be formed, for example, from a pair of thin, continuous layers (a backsheet and a topsheet) of a polymer film and/or non-woven web that retain a series of individual, absorbent cores that are spaced evenly apart along the longitudinal axis of the web. The process may include cutting each absorbent article from the continuous web of material, folding the pair of wings around the central portion, applying an adhesive to a release tape, and attaching the release tape to the wings (not necessarily in that order). The wearer removes this release tape to expose the adhesive that has transferred to the backsheet in order to attach the wings to the undergarment.

During the step of folding the pair of wings around the central portion, the article may be conveyed over one or more stationary, contoured rails, which are known in the art as folding plows or folding boards. The folding plows gradually fold each wing 180 degrees from the original plane of the conveyed, web material. Ideally, the wings are consistently folded along fold lines that are parallel to the longitudinal axis of the article so that the free ends of the folded wings come together approximately edge-to-edge.

Unfortunately, sometimes during the folding step, one or both of the wings of an article are folded into a skewed configuration, thereby resulting in a gap between the edges of the free ends of the wings. Generally, manufactured articles having this "skew" also may be excessively wrinkled or may have irregular folds. Similarly, one or both wings may fold-over on itself, either inwardly or outwardly. In either the skew or the fold-over situation, it is possible for some of the adhesive on the release tape to transfer to the topsheet that eventually comes into contact with the wearer's body, causing her considerable discomfort.

Accordingly, there is a need for an improved folding system and process for folding the wings of absorbent articles as they are manufactured from a continuous moving web, whereby wing-folding skew and fold-over are minimized.

Conventional methods for detecting folding process variations in a cost-effective manner have been only partially successful. For example, vision systems have been adapted for use on production lines of absorbent articles to detect product defects such as wings having skewed configurations. However, using the vision systems does not always lead to elimination of the root cause of the problem. Even when skewing is detected, significant production time may be lost in finding the source of the problem and making the necessary repairs and/or design modifications. Traditionally, many types of process and production line component improvements in such manufacturing environments are accomplished using highly iterative, physical testing/prototyping methods, which may be very costly. In addition, it may not always be possible to easily observe or appreciate the effects of the numerous, complex, physical phenomena that may be occuring during the high speed production of absorbent articles. For the folding process described above, such phenomena may include inertial loading on the conveyed articles, changing material properties, aerodynamic forces and friction, especially at interfaces between the conveyed articles and the folding plows.

Accordingly, there is also a need for a method of analyzing the folding system during operation, especially for predicting the magnitude of wing-folding skew, and for optimizing the design of the folding system and process.

SUMMARY OF THE INVENTION

A folding system is provided for folding at least one wing extending from a central portion (also referred to as a central chassis) of each of a plurality of absorbent articles formed from a continuous moving web moving in a longitudinal direction. The folding system includes a wing-folding conveyor that holds the central chassis of each absorbent article and moves each absorbent article in the longitudinal direction. The folding system also includes at least one elongated, folding plow mounted alongside the wing-folding conveyor. The folding plow has an entrance end, an exit end and an inner edge that define a twist axis that is parallel to the longitudinal direction. The folding plow also has a contoured surface having a configuration defined by a twist angle that increases along the twist axis from zero degrees near the entrance end to 180 degrees near the exit end. The twist angle is formed by the intersection between a first plane containing the central chassis and a second plane containing the contoured surface and may be measured in a twist angle plane section transverse to the twist axis for any location along the twist axis. The wing-folding conveyor moves the central chassis along the inner edge of the folding plow and the wing slides against the contoured surface from the entrance end to the exit end, such that the wing folds around the central chassis near the inner edge.

In another embodiment, a folding system includes a wing-folding conveyor that holds the central chassis of each absorbent article and moves each absorbent article in the longitudinal direction. The folding system also includes at least one elongated, folding plow mounted alongside the wing-folding conveyor. The folding plow has an entrance end, an exit end and an inner edge that define a twist axis that is parallel to the longitudinal direction, and a contoured surface having a configuration defined by a twist angle that increases along the twist axis from zero degrees near the entrance end to 180 degrees near the exit end. The twist angle is formed by the intersection between a first plane containing the central chassis and a second plane containing the contoured surface and may be measured in a twist angle plane section transverse to the twist axis for any location along the twist axis. The folding system also includes at least one blower positioned near the wing-folding conveyor and generating a gas flow impinging upon the absorbent article, thereby helping to hold the wing against the folding plow. The wing-folding conveyor moves the central chassis along the inner edge of the folding plow and the wing slides against the contoured surface from the entrance end to the exit end, such that the wing folds around the central chassis near the inner edge.

A method is also provided for analyzing the operation of a folding system that may be used for folding at least one wing extending from a central chassis of each of a plurality of absorbent articles formed from a continuous moving web moving in a longitudinal direction. The folding system includes a wing-folding conveyor that holds the central chassis of each absorbent article and moves each absorbent article in the longitudinal direction, and at least one elongated, folding plow mounted alongside the wing-folding conveyor. The folding plow has an entrance end, an exit end and an inner edge that define a twist axis that is parallel to the longitudinal direction. The folding plow also has a contoured surface having a configuration defined by a twist angle that increases along the twist axis from zero degrees near the entrance end to 180 degrees near the exit end, wherein the twist angle is formed by the intersection between a first plane containing the central chassis and a second plane containing the contoured surface and may be measured in a twist angle plane section transverse to the twist axis for any location along the twist axis. The folding system also includes at least one blower positioned near the wing-folding conveyor and generating a gas flow impinging upon the absorbent article, thereby helping to hold the wing against the folding plow. The wing-folding conveyor moves the central chassis along the inner edge of the folding plow and the wing slides against the contoured surface from the entrance end to the exit end, such that the wing folds around the central chassis near the inner edge. The method includes providing values for input parameters related to the folding system and a folding process, performing a computational flow analysis on the gas flows generated by the blower, calculating an approximate gas pressure on each absorbent article as a function of position and time, performing a finite element analysis of the absorbent article sliding along the folding plow and generating output parameters related to the performance of the folding system during operation.

Other aspects, variations, and embodiments of the an improved folding system and method of analyzing the operation of a folding system will become apparent from the following description, the accompanying drawings, and the appended claims.

BRIEF DESCRIPTION OF THE DRAWINGS

FIG. 2 is a top view of a folded pad having a wing-fold skew;

FIG. 3 is an end view of the pad shown in FIG. 2;

FIG. 4 is a top view of a properly folded pad;

FIG. 5 is an end view of the pad shown in FIG. 4;

FIG. 17 is a top view of an original, drive side folding plow;

FIG. 18 is a top view of an improved, drive side folding plow;

FIG. 23 is a detailed, bottom isometric view of a portion of the drive side folding plow shown in FIG. 11;

FIG. 24 is a detailed, bottom isometric view of a portion of the drive side folding plow shown in FIG. 12;

FIG. 37 is an isometric view of a rotary knife;

FIG. 38 is a partial, cross-sectional view taken at line 38-38 of the rotary knife shown in FIG. 37;

FIG. 41 is a schematic illustration showing a lay-out of the folding system and a plurality of parameters that may be relevant to the method shown in FIG. 40.

DETAILED DESCRIPTION OF THE INVENTION

An improved folding system and process is provided for the high-volume production of folded, absorbent articles such as sanitary napkins and panty liners. As will be described next, the folding system includes numerous improvements that, in combination, reduce undesirable wrinkling and skewing of the pads, particularly the wings when folded during operation. The improved folding system and process also reduces the occurrence of fold-over (in both the inward and outward directions) of wings or flaps of such absorbent articles. A method for analyzing the folding system during operation is also provided. The method may be used to predict the performance of the folding system during operation, and to optimize the design of the system and process.

It should be understood that the folding system and process described herein refers to the folding of discrete, absorbent articles that have been formed and cut from a continuous moving web, and that such absorbent articles may also include adult and baby diapers, facial tissues, and other implements having folds.

Overview of the Folding System and Process

Figure 1:
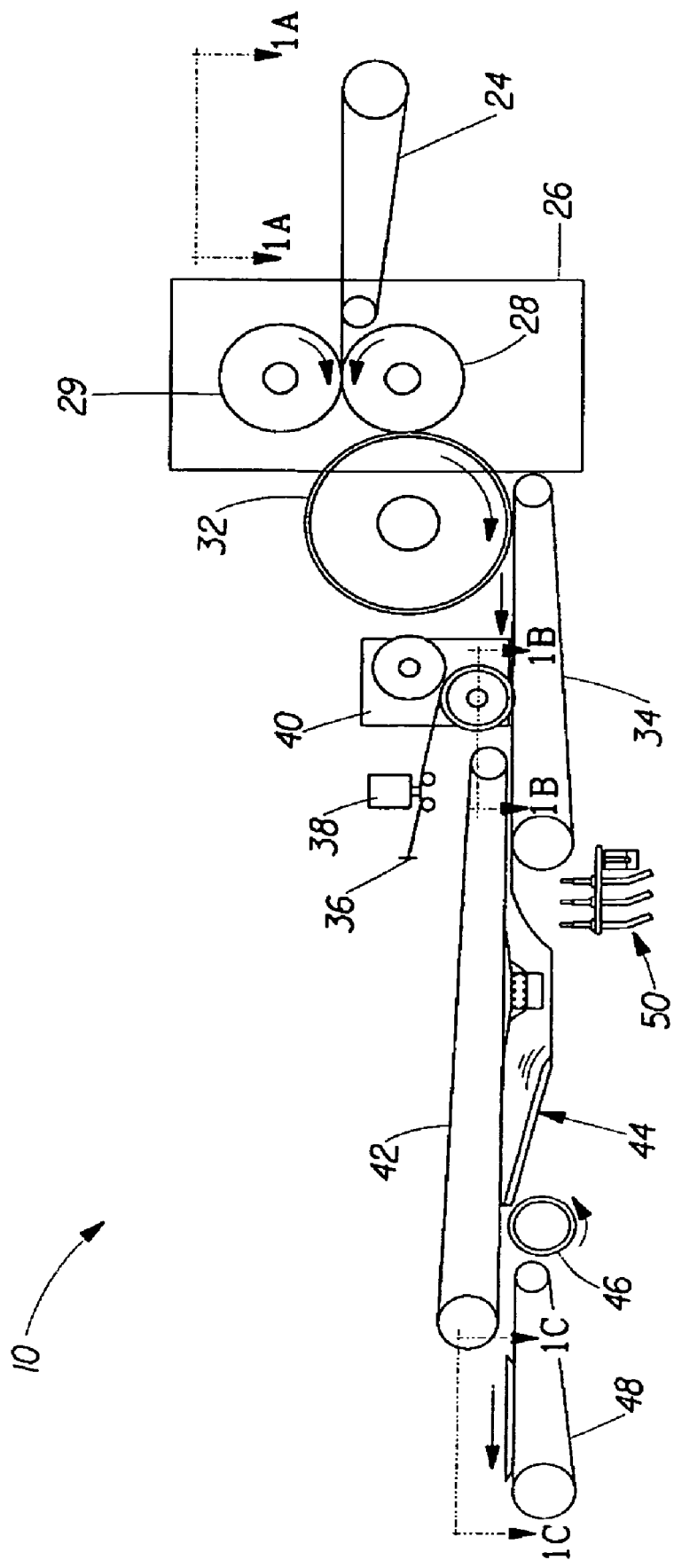
FIG. 1 is a schematic illustration of a folding system that may be used in a folding process.

FIG. 1 is a schematic illustration of a folding system, generally designated 10, that conveys a continuous web 12, cuts each absorbent article 20 (also referred to as a pad 20) from web 12 at a rate of several hundred pads per minute, applies a release tape 16 having an adhesive to each pad 20, and folds each pad 20 into a folded configuration for further processing and/or packaging. Web 12 may include a perforated film or non-woven web topsheet and a liquid impervious backsheet, each of which may be formed from a thin polymer film or non-woven webs as is well-known in the art of making disposable absorbent products. Web 12 may be approximately 200 millimeters wide and fed off a roll (not shown) to folding system 10. A continuous series of elongated, pad cores 15 (view A-A) are aligned end-to-end along a longitudinal web axis 22 of web 12 and spaced evenly apart. Each pad core 15 may be any of known materials and configurations for absorbent cores in sanitary napkins, panty liners and other absorbent articles. Such absorbent materials include paper, cotton and/or other suitable synthetic or natural products,. Each pad core 15 is retained between the top and backsheets, as is well-known in the art, to form a central chassis 14 (view C-C) having a pair of longitudinal side edges 17.

Folding system 10, like many industrial conveyor systems, has a drive side and an operator side. In FIG. 1, folding system 10 is viewed from the operator side, and the flow of web 12 is from right to left. Web 12 is conveyed along a first vacuum conveyor 24 (also referred to as an input conveyor) that is perforated and in fluid communication with a vacuum source (not shown) such that the topsheet of web 12 is held against conveyor 24, as is well-known in the art. Web 12 next is conveyed through a cutting assembly 26 having a rotary knife 28 that cuts the individual absorbent articles 20 from web 12. (For description purposes, an individual pad shall often be referred to herein, although it should be kept in mind that during steady-state production, tens of pads are formed each second.) Absorbent articles can have flaps to be folded, such as ear flaps of a disposable absorbent diaper. In one embodiment disclosed herein flaps are wings of a sanitary napkin. A first wing 30 and a second wing 31 are formed on opposite sides of central chassis 14. Pad 20 is next transferred by a transfer roll 32 to the top of a second vacuum conveyor 34 (also referred to as a transfer conveyor). Above second vacuum conveyor 34, an adhesive applicator 38 intermittently applies an adhesive to a continuous tape 36, which then passes through a phase-driven, cut-and-slip knife 40 to form a continuous series of individual release tapes 16 with adhesive. One end of each release tape 16 is then bonded to the backsheet of second wing 31 of each pad 20, allowing the free end of release tape 16 to extend laterally beyond wing 31. Pad 20 is next conveyed from the top of second vacuum conveyor 34 to the bottom of a third vacuum conveyor 42 which can also be referred to as a flap-folding conveyor for disposable articles, or specifically a wing-folding conveyor for winged sanitary napkins.

Pad 20 is conveyed by third vacuum conveyor 42 so that wings 30, 31 slide against a pair of folding plows 44, also referred to as folding rails or folding boards, in order to fold each of wings 30, 31 around central chassis 14 to form the folded pad configuration shown in view C-C. As will be described, the configurations of folding plows 44 are particularly important relevant to folding wings 30, 31 on pad 20 without undesirable wrinkling and skewing. As pad 20 is conveyed along folding plows 44, a plurality of blowers 50 positioned beneath plows 44 provide a positive air pressure profile to help hold wings 30, 31 against plows 44. Pad 20 is next conveyed through a bonding roll 46 to press release tape 16 against wings 30, 31 so that the adhesive on release tape 16 bonds completely to wings 30, 31. Pad 20 next is conveyed from the bottom of third vacuum conveyor 42 to the top of a fourth vacuum conveyor 48 (also referred to as an output conveyor), from where pad 20 may be conveyed to subsequent processes.

FIG. 2 is a top view and FIG. 3 is an end view, showing a pad plane 15, of an improperly folded pad 20. FIG. 4 is a top view and FIG. 5 is an end view of a properly folded pad 20. In FIG. 4, second wing 30 is shown to have an edge 52 approximately aligned along longitudinal web axis 22 and first wing 31 is shown to have an edge 54 that is also aligned with longitudinal web axis 22 and touching or nearly touching edge 52 at a longitudinal pad axis 23. A slight overlap of edges 52, 54 may also be considered to be acceptable. However, for the improperly folded pad 20 shown in FIG. 2, edge 54 of first wing 31 is angled with respect to longitudinal pad axis 23, thereby resulting in a wing gap "W" and a skew "S". One side of release tape 16 has a first corner 56 that is closer to longitudinal pad axis 23 than a second corner 58. Skew shall be defined herein as the difference in distance from longitudinal pad axis 23 of first corner 56 and second corner 58. Skew has been observed for some folding processes to be in the range of about 1 to 6 millimeters. As noted earlier, when pad 20 is improperly folded with a skew greater than about 2 millimeters, it is possible for some adhesive on release tape 16 to transfer to the topsheet of pad 20, thereby possibly resulting in the undesirable situation of adhesive sticking to the body of the wearer. Skew may also be accompanied by undesirable wrinkling of pad 20. As disclosed herein, folding system 10 provides for the high-volume manufacture of pads 20 having minimal skewing, fold-over and wrinkling.

Configuration of Folding Plows

Figure 6:
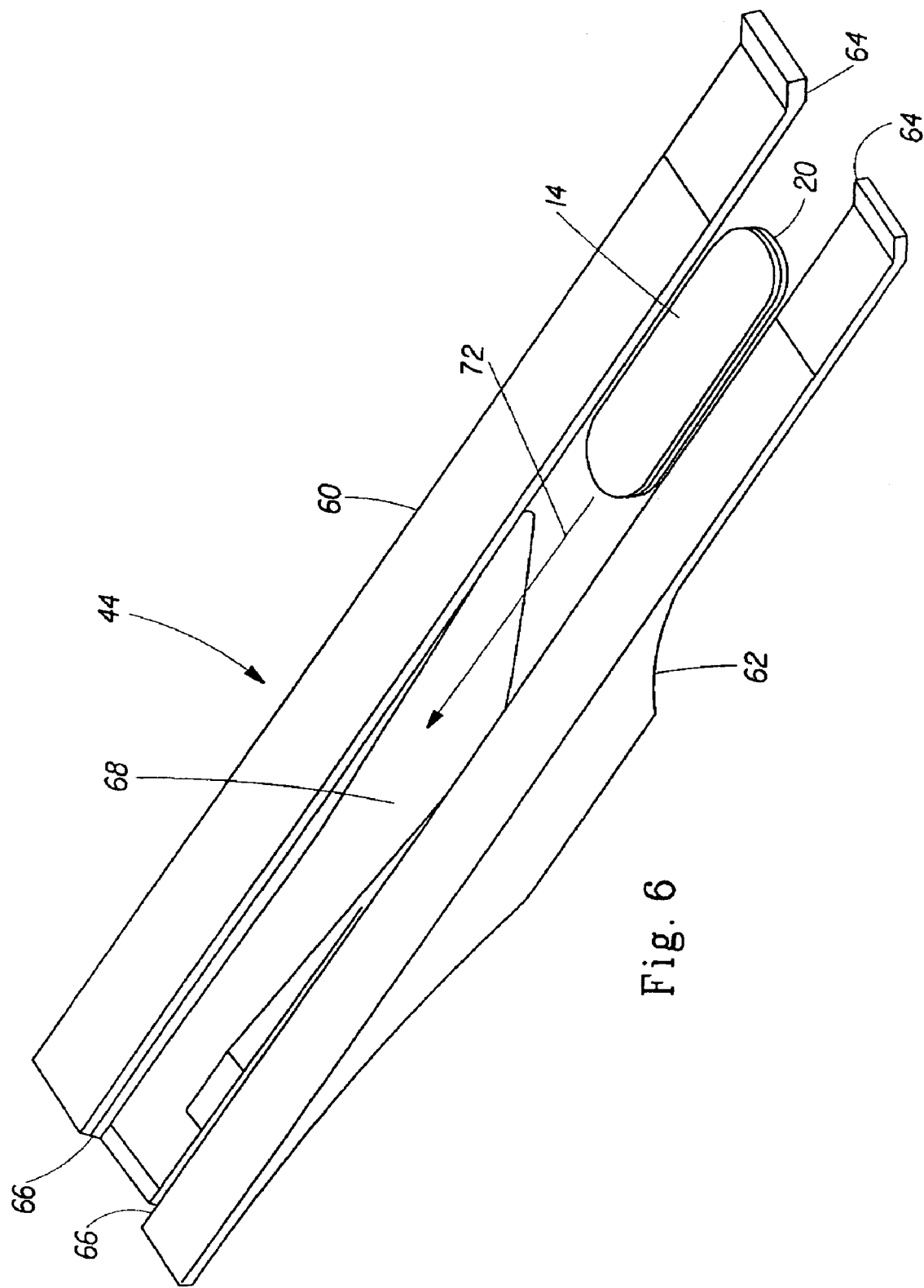
FIG. 6 is an isometric, top view of a pair of folding plows of the folding system shown in FIG. 1.
Figure 7:
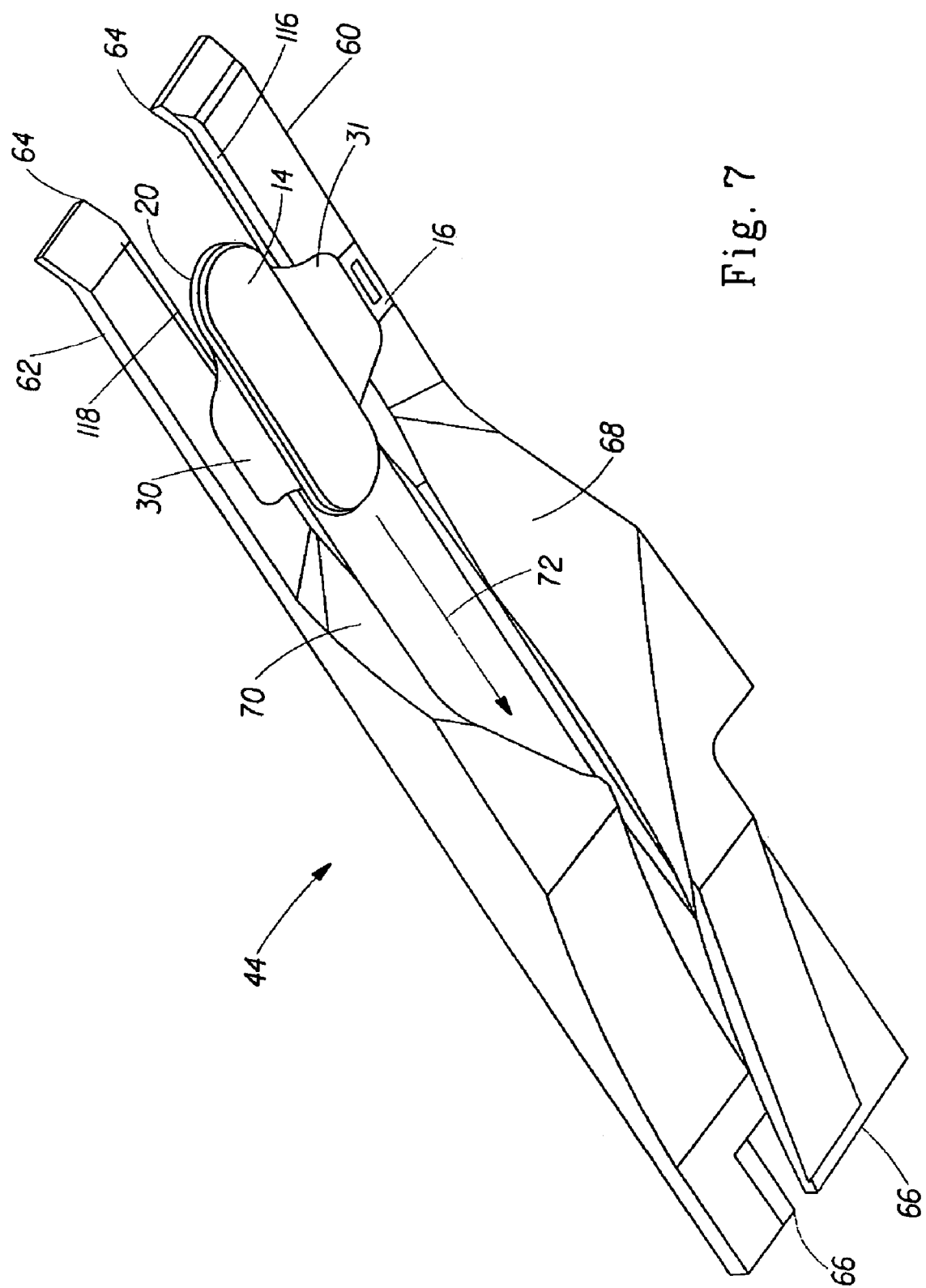
FIG. 7 is an isometric, bottom view of the pair of folding plows shown in FIG. 6.

FIG. 6 is a top isometric view and FIG. 7 is a bottom isometric view of folding plows 44, which include a drive side plow 60 and an operator side plow 62. Pad 20 is conveyed along folding plows 44 by third vacuum conveyor 42 (FIG. 1) in the direction indicated by arrow 72. Each of folding plows 44 may be formed from a metal or other hard, rigid, wear-resistant material that may be formed with a smooth surface. Folding plows 44 may also be coated with a lubricious and/or wear resistant material to reduce friction at the interfaces with pad 20. The length of folding plows 44 may vary significantly, but may be approximately in the range of 25 to 100 centimeters. Drive side plow 60 and operator side plow 62 are mounted beneath third conveyor 42 and are parallel and spaced apart to define a plow entrance 64 and a plow exit 66. Drive side plow 60 has a contoured surface 68 that contacts the backsheet side of wing 31 and release tape 16 of pad 20, as shown in FIG. 7. Operator side plow 62 has a contoured surface 70 that contacts the backsheet side of wing 30 of pad 20. As is well-known in the art, contoured surface 70 is shaped to fold wing 30 around central chassis 14 before contoured surface 68 completes the folding of wing 31 around central chassis 14 so that release tape 16 may be bonded to the backsheet side of folding wing 30 at the end of the folding process.

Figure 8:
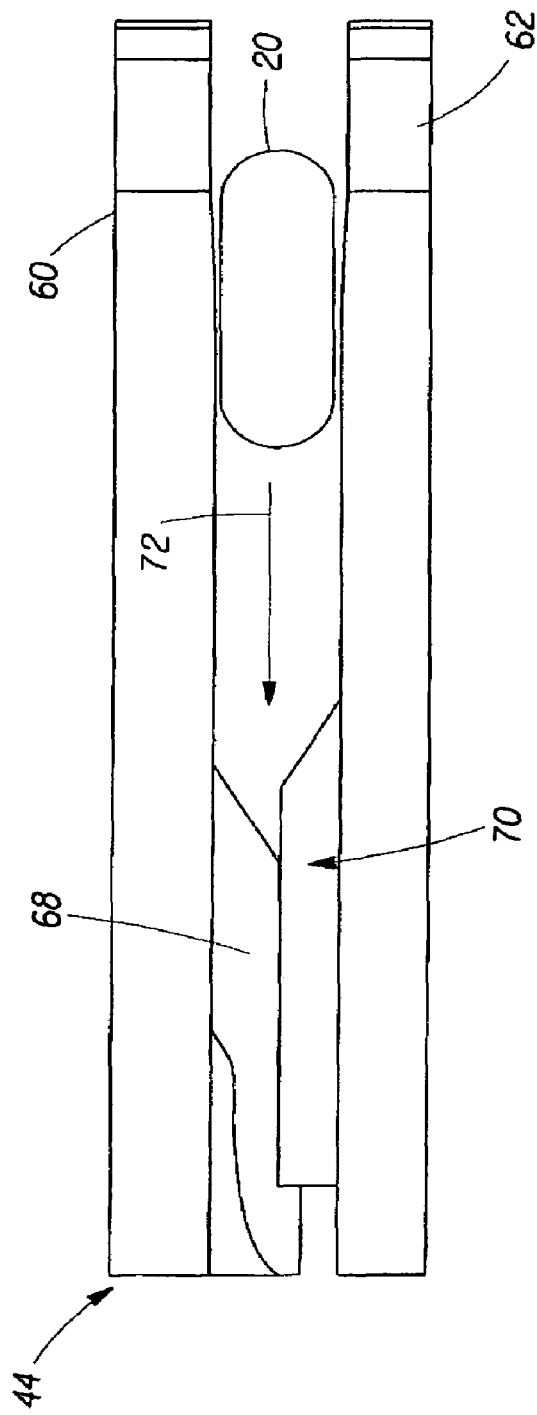
FIG. 8 is a top view of the pair of folding plows shown in FIG. 6.
Figure 9:
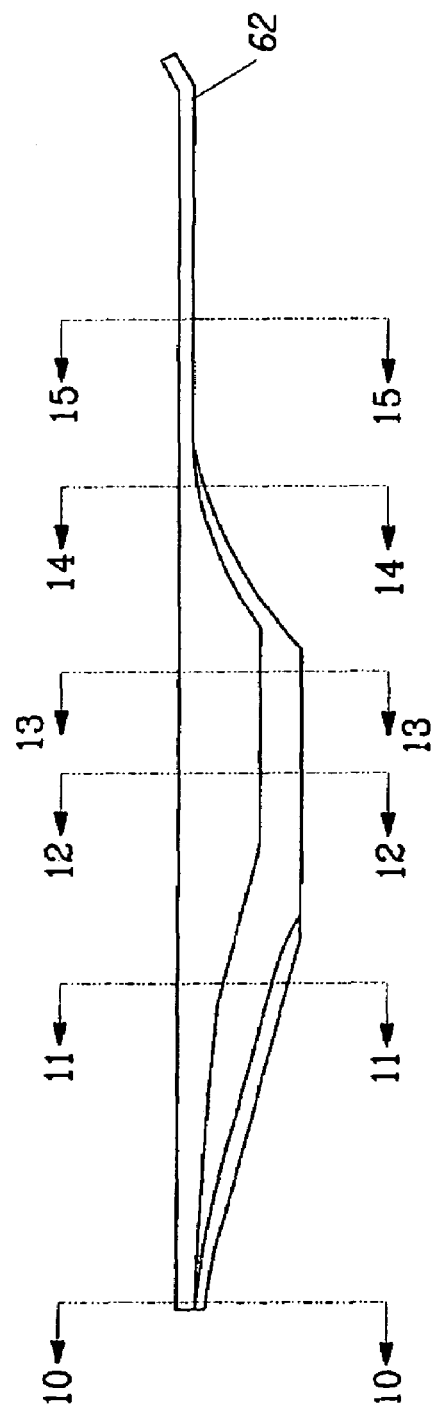
FIG. 9 is an operator side view of the pair of folding plows shown in FIG. 6.
Figure 10:
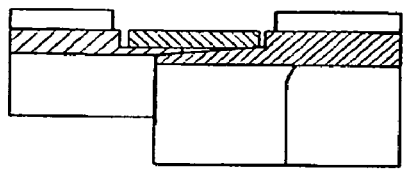
FIG. 10 is a cross-sectional view taken at line 10-10 of the folding plows shown in FIG. 6.
Figure 13:
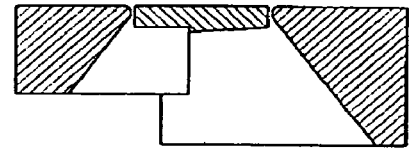
FIG. 13 is a cross-sectional view taken at line 13-13 of the folding plows shown in FIG. 6.
Figure 11:
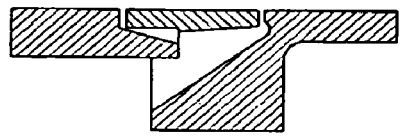
FIG. 11 is a cross-sectional view taken at line 11-11 of the folding plows shown in FIG. 6.
Figure 14:
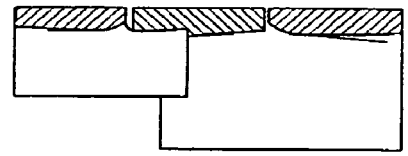
FIG. 14 is a cross-sectional view taken at line 14-14 of the folding plows shown in FIG. 6.
Figure 12:
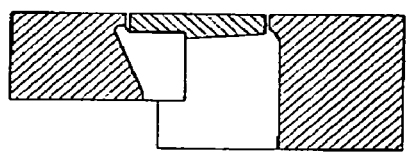
FIG. 12 is a cross-sectional view taken at line 12-12 of the folding plows shown in FIG. 6.
Figure 15:
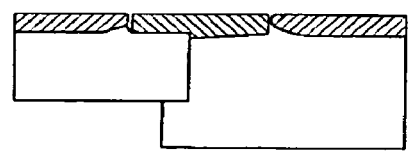
FIG. 15 is a cross-sectional view taken at line 15-15 of the folding plows shown in FIG. 6.

FIG. 8 is a top view of folding plows 44, showing operator side plow 62 and a portion of contoured surface 70, and showing drive side plow 60 and a portion of contoured surface 68. Pad 20 is conveyed from right to left as indicated by arrow 72. FIG. 9 is an operator side view of folding plows 44. FIG. 10 is a cross-sectional view taken at line 10-10, FIG. 11 is a cross-sectional view taken at line 11-11, FIG. 12 is a cross-sectional view taken at line 12-12, FIG. 13 is a cross-sectional view taken at line 13-13, FIG. 14 is a cross-sectional view taken at line 14-14, and FIG. 15 is a cross-sectional view taken at line 15-15 of the folding plows shown in FIG. 6. As will be described for FIGS. 27 through 32, folding plows 44 are configured such that the inertial loading effects on pad 20 are significantly mitigated relative to a pair of original folding plows without the improved configurations, thereby reducing process variations that may result in wing-folding skew and fold-over.

Figure 16:
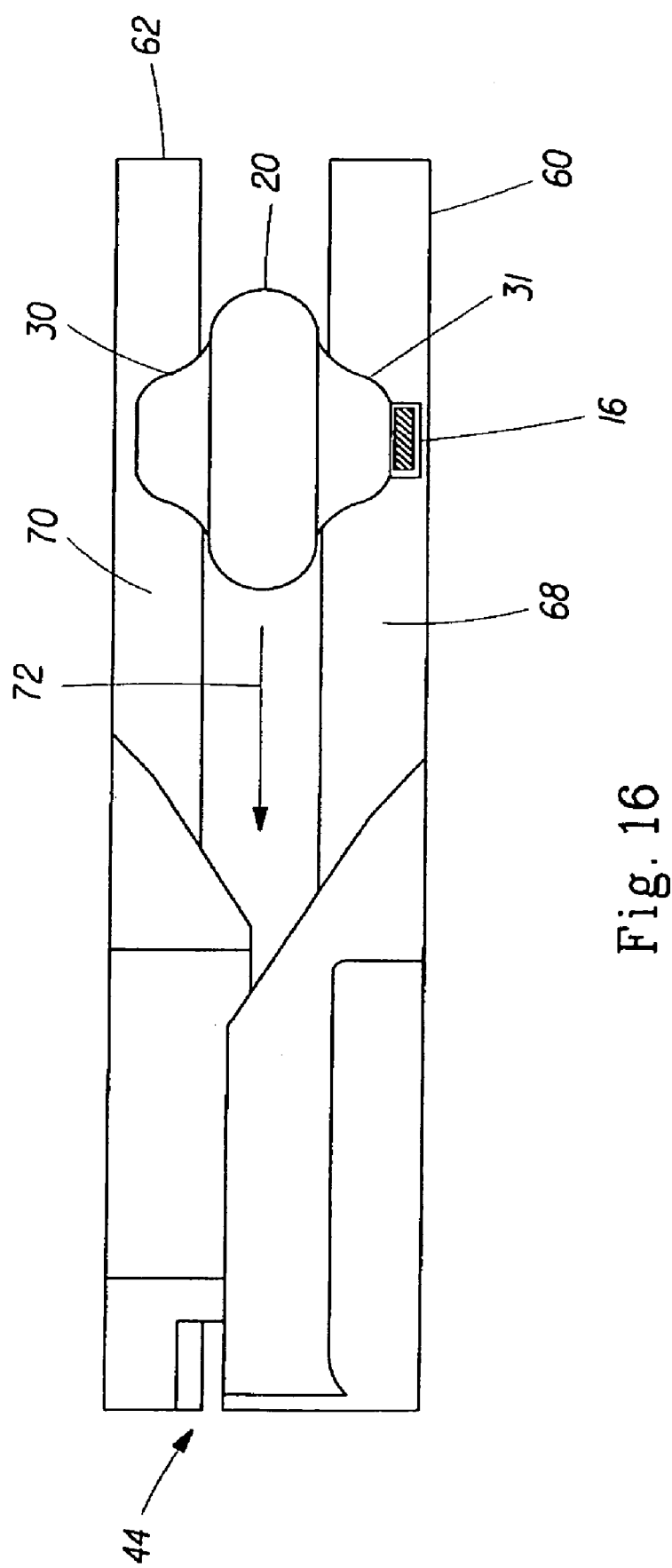
FIG. 16 is a bottom view of the pair of folding plows shown in FIG. 6.

FIG. 16 is a bottom view of folding plows 44, showing first wing 31 and release tape 16 sliding against contoured surface 68 of drive side plow 60, and second wing 30 sliding against contoured surface 70 of operator side plow 62. The additional mass of release tape 16 extending from wing 31 contributes to the frictional, aerodynamic and inertial loading effects acting on wing 31. Therefore, it is not uncommon for wing 31 to skew during the folding process more often than wing 30.

FIG. 17 is a bottom view of an original, drive side plow 74. Central chassis 14 of pad 20 (not shown) closely follows along an inner edge 82 that defines a twist axis 75, about which wing 31 "twists" during the folding process. Twist axis 75 is approximately parallel to longitudinal web axis 22 (FIG. 1). Original plow 74 has a flat surface 77 that is approximately parallel to pad plane 15 (FIG. 2) and to the bottom surface of third vacuum conveyor 42. Flat surface 77 intersects with contoured surface 76 to define a transition corner 79 that is oriented at an angle "Q1" with respect to twist axis 75. Q1 for drive side plow 74 is approximately 90 degrees.

FIG. 18 is a bottom view of improved, drive side plow 60 with contoured surface 68 and an inner edge 80 that defines a twist axis 61. Improved plow 60 has a flat surface 67 that intersects with contoured surface 68 to define a transition corner 69 that is oriented an angle "Q2" with respect to twist axis 75. Q2 is shown in FIG. 12 to be approximately 45 degrees, but Q2 may be approximately in the range of 30 to 60 degrees. Transition corner 69 intersects inner edge 80 at an inner transition point 88 and intersects an outer edge 81 at an outer transition point 90. An angular offset "X" is the longitudinal distance between inner transition point 88 and outer transition point 90.

FIG. 23 is a detailed, bottom isometric view of a portion of original plow 74. A twist angle plane section 84 is shown at an arbitrarily selected location through contoured surface 76. Twist angle plane section 84 is parallel to transition corner 79 and contains a twist angle "TA1" that is the angle between contoured surface 76 and the plane containing flat surface 82. TA1 increases from approximately zero to approximately 180 degrees along contoured surface 76 in the conveying direction (also referred to as the machine direction).

FIG. 24 is an enlarged, bottom isometric view of improved plow 60. A twist angle plane section 86 is shown at an arbitrarily selected location through contoured surface 68. Twist angle plane section is parallel to transition corner 69 and contains a twist angle "TA2" that is the angle between contoured surface 68 and the plane containing flat surface 67. TA2 increases from approximately zero to approximately 180 degrees along contoured surface 68 in the conveying direction. Angular offset X may be maintained for each twist angle plane section along the length of contoured surface 68.

Orienting twist angle plane 86 to provide angular offset X, as shown in FIG. 24, allows improved plow 60 to begin to fold the portion of wing 31 near edge 80 (and closest to central chassis 14) before folding the portion of wing 31 near outer edge 81. This arrangement provides a sort of "angular bias" to release tape 16 and smoothes the transition of wing 31 as it is conveyed from flat surface 67 to contoured surface 68.

Figure 19:
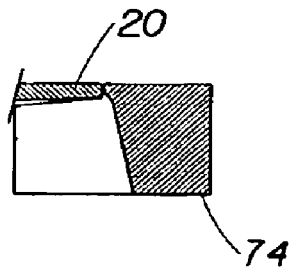
FIG. 19 is a cross-sectional view taken at line 19-19 of the drive side folding plow shown in FIG. 11, shown with a partial, cross-sectional view of a pad.
Figure 20:
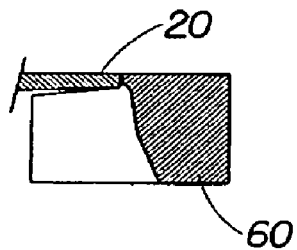
FIG. 20 is a cross-sectional view taken at line 20-20 of the drive side folding plow shown in FIG. 12, shown with a partial, cross-sectional view of a pad.
Figure 21:
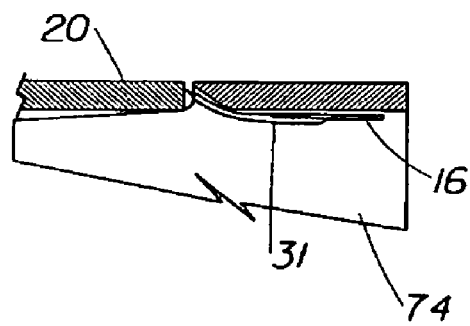
FIG. 21 is a cross-sectional view taken at line 21-21 of the drive side folding plow shown in FIG. 11, shown with a partial, cross-sectional view of a pad.
Figure 22:
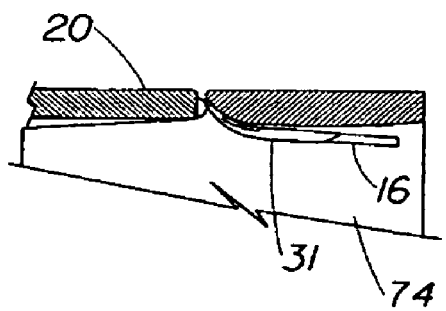
FIG. 22 is a cross-sectional view taken at line 22-22 of the drive side folding plow shown in FIG. 12, shown with a partial, cross-sectional view of a pad.

FIG. 19 is a cross-sectional view taken at line 19-19 of original, drive side plow 74 shown in FIG. 17, shown with a partial, cross-sectional view of pad 20. FIG. 20 is a partial, cross-sectional view taken at line 20-20 of improved, drive side plow 60 shown in FIG. 18, shown with a partial, cross-sectional view of pad 20. FIG. 21 is a cross-sectional view taken at line 21-21 of original, drive side plow 74 shown in FIG. 17, shown with a partial, cross-sectional view of pad 20. FIG. 22 is a partial, cross-sectional view taken at line 22-22 of improved, drive side plow 60 shown in FIG. 18, shown with a partial, cross-sectional view of pad 20. As may be seen in FIGS. 19 through 22, orienting the twist angle planes so that Q2 is in the range of 30 to 60 degrees results in compound curvatures on contoured surface 68 that, together with angular offset X, provide a "rolling-fold" action of wing 31 as it is conveyed along plow 60. This configuration reduces abrupt impacts on wing 31 and release tape 16 that may result in skewing, fold-over and wrinkling of pad 20. As will be apparent to those skilled in the art, the twist angle planes may also be oriented on operator side plow 62 to be approximately in the range of 30 to 60 degrees to obtain similar beneficial effects.

Figure 25:
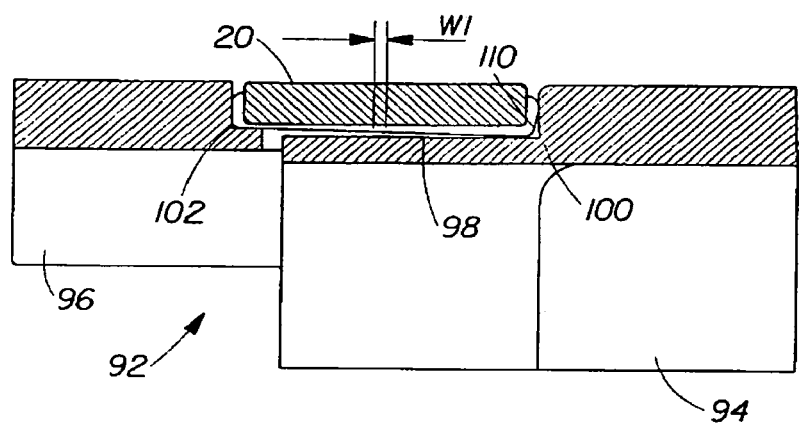
FIG. 25 is a cross-sectional view taken near an exit end of the drive side folding plow shown in FIG. 11, and shown with a cross-sectional view of the pad and an operator side folding plow.
Figure 26:
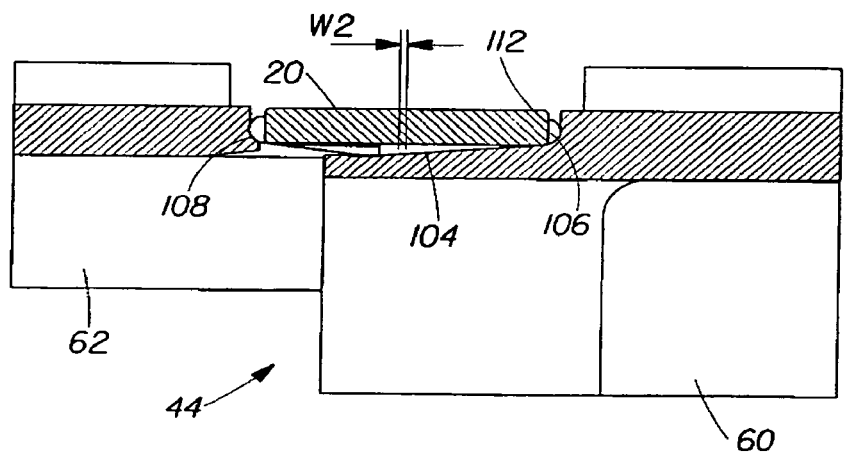
FIG. 26 is a cross-sectional view taken at an exit end of the drive side folding plow shown in FIG. 12, and shown with a cross-sectional view of the pad and an operator side folding plow.

FIG. 25 is a cross-sectional view of a pair of original, folding plows 92, taken at a location near the exit end. A drive side plow 94 and an operator side plow 96 define a throat region 98. At this stage of the folding process, pad 20 is nearly in its final, folded configuration prior to transfer through bonding roll 46 (FIG. 1). A sharp inside corner 100 (approximately less than 2 millimeters radius) on drive side plow 94 and a sharp inside corner 102 on operator side plow 96 provide an unpredictable folding path for pad 20, thereby frequently resulting in an undesirable wing gap "W1" as shown in FIG. 25. FIG. 26 is a cross-sectional view of improved folding plows 44 near exit end 66 (FIG. 7). Drive side plow 60 and operator side plow 62 form a throat region 104. An inside corner 106 on drive side plow 60 and an inside corner 108 on operator side plow 62 are generously radiused to provide an improved folding path, resulting in reduced folding variability and a wing gap "W2" that is consistently smaller than W1 in FIG. 25. Each of inside corners 106 and 108 may have a radius approximately in the range of 2 to 10 millimeters.

Folding plows 44 are configured to fold pad 20 during the high-volume, folding process consistently with minimal skewing, fold-over and wrinkling. The particular configuration of folding plows 44 disclosed herein was derived from mathematical simulations combined with physical prototyping and testing. As noted earlier, there are numerous factors that may be considered in an analysis of the folding process, but a key factor is the inertial loading effects on pad 20 as it is conveyed over folding plows 44. As pad 20 is conveyed along folding plows 44 and wings 30, 31 are folded inwardly around central chassis 14, the mass of wings 30, 31 accelerate and decelerate. It is possible to reduce folding process variation by minimizing the peak accelerations and decelerations of wings 30, 31 as they are folded from the pad plane (zero degrees) to their final folded orientation (180 degrees from the pad plane.) This "smoothing-out" of the folding process may be observed mathematically for various configurations of folding plows 44. A desired configuration may then be incorporated into the actual design of the folding plows and used in folding system 10.

FIGS. 27 through 32 are graphs that show a comparison between a pair of original folding plows having a conventional configuration and a pair of improved folding plows having an improved configuration such as described for folding plows 44 in FIG. 8. The position, velocity and acceleration of the twist angle as a function of time are shown for both the operator side and the driver side folding plows. The time shown represents the time during which the wing of the pad slides along the contoured surface of the folding plow. If the velocity in the longitudinal direction of the conveyor is known, the time axis may be easily converted to a distance-traveled axis for each of the graphs, indicating the longitudinal position of the pad along the contoured surface.

Figure 27:
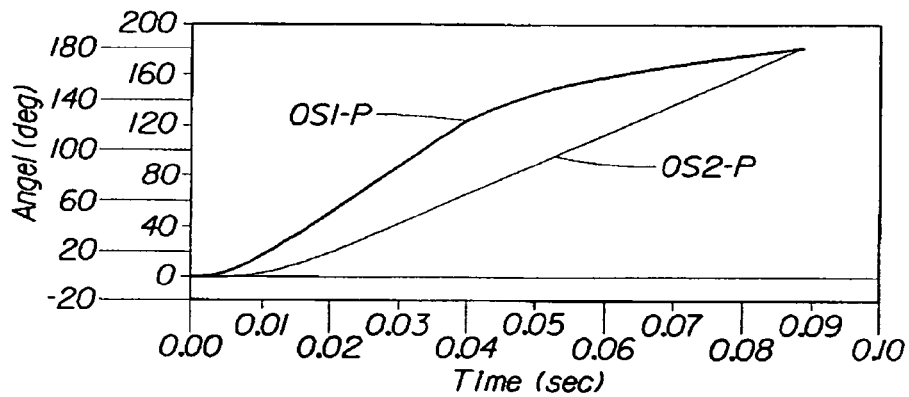
FIG. 27 is a graph of twist angle versus time showing curves corresponding to the original and improved operator side folding plows, as predicted by a mathematical model.

FIG. 27 is a graph showing twist angle (degrees) versus time (seconds) as one wing of the pad is conveyed along the contoured surface of the operator side plow. A curve "OS1-P" corresponds to an original, operator side plow prior to optimization for inertial loading effects. A curve "OS2-P" corresponds to an improved, operator side plow such as operator side plow 62 shown in FIG. 7. The twist angles were derived from mathematical models of the contoured surfaces of the original and improved plows. As may be seen in FIG. 27, curve OS1-P is non-linear, showing a marked "hump" around 0.05 seconds. Curve OS2-P, however, is approximately linear between 0.02 and 0.08 seconds, after a gradual slope increase between zero and 0.02 seconds.

Figure 28:
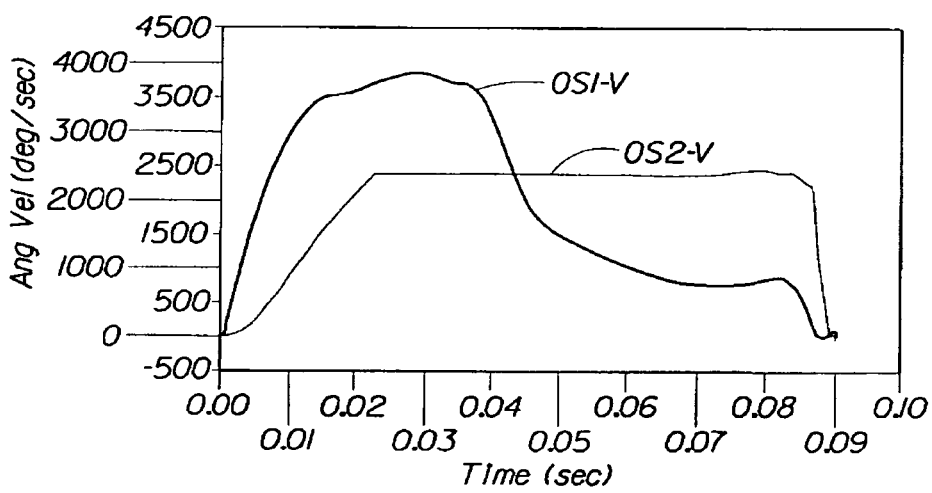
FIG. 28 is a graph of twist angular velocity versus time showing curves corresponding to the original and improved operator side folding plows, as predicted by the mathematical model.

FIG. 28 is a graph showing twist angle velocity (degrees/second) versus time. A curve "OS1-V" is the first mathematical derivative of curve OS1-P in FIG. 27. A curve "OS2-V" is the first mathematical derivative of curve OS2-V in FIG. 27.

As shown in FIG. 28, the angular velocity of the wing depicted in OS1-V during the first portion of the folding process is very high, exceeding 3500 degrees per second, and then decreases rapidly during the last portion of the folding process. OS2-V, however, has a relatively "flat" velocity profile during most of the wing folding.

Figure 29:
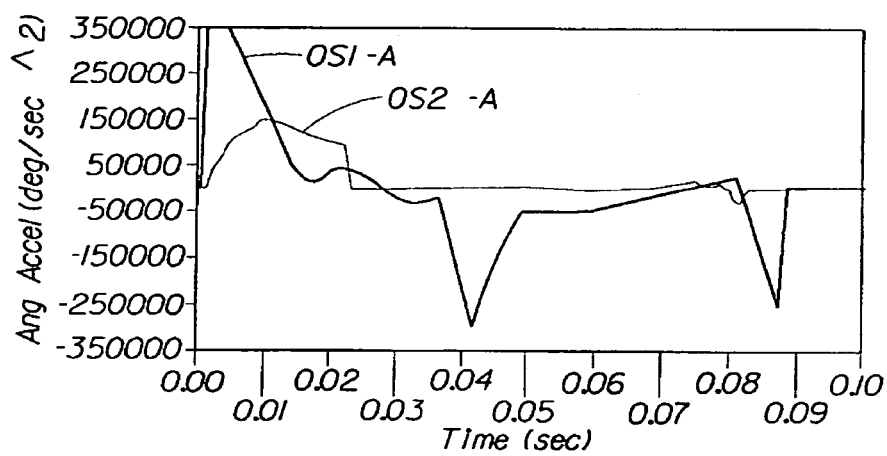
FIG. 29 is a graph of twist angular acceleration versus time showing curves corresponding to the original and improved operator side folding plows, as predicted by the mathematical model.
Figure 30:
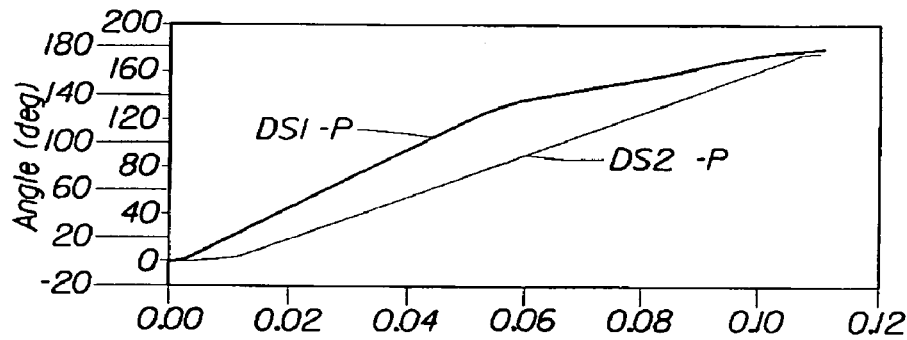
FIG. 30 is a graph of twist angle versus time showing curves corresponding to the original and improved drive side folding plows, as predicted by the mathematical model.
Figure 31:
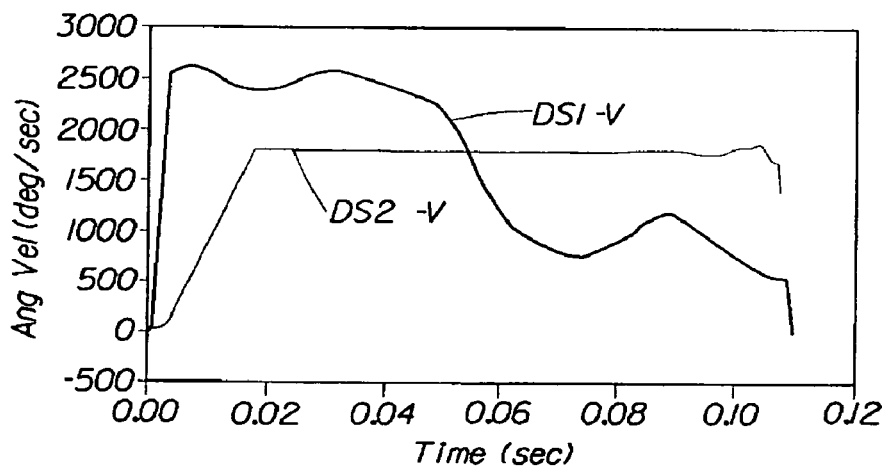
FIG. 31 is a graph of twist angular velocity versus time showing curves corresponding to the original and improved drive side folding plows, as predicted by the mathematical model.
Figure 32:
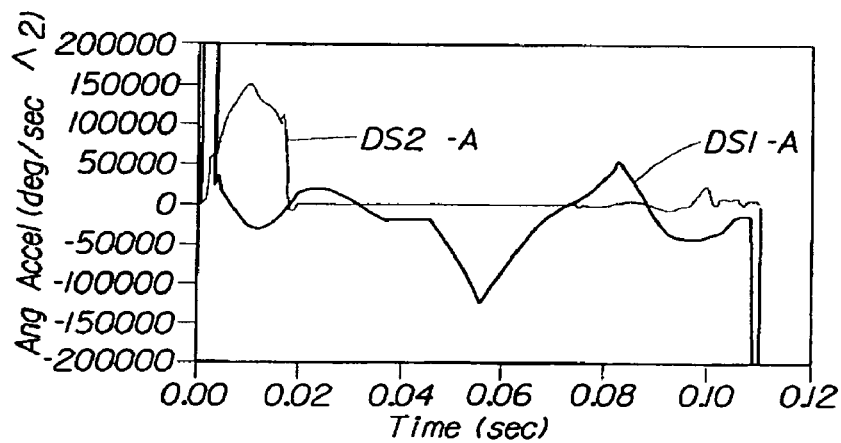
FIG. 32 is a graph of twist angular acceleration versus time showing curves corresponding to the original and improved drive side folding plows, as predicted by the mathematical model.

FIG. 29 is a graph showing twist angle acceleration (degrees/second$^2$) versus time. A curve "OS1-A" is the second mathematical derivative of curve OS1-P in FIG. 27. A curve "OS2-A" is the second mathematical derivative of curve OS2-P" in FIG. 27. FIG. 29 shows the acceleration of the wing depicted in OS1-A to far exceed 350,000 degrees/second$^2$, and decelerations to exceed −250,000 deg./sec.$^2$ However, the wing depicted in OS2-A does not have any peak accelerations or decelerations outside of the range of approximately −50,000 to 150,000 deg./sec.$^2$ FIG. 30, FIG. 31, and FIG. 32 were derived mathematically in the same manner as for FIG. 27, FIG. 28, and FIG. 29, respectively, except that the initial twist angle data was derived from mathematical models of the drive side plows. The twist angle, twist angle velocity, and twist angle acceleration corresponding with the original drive side plow are designated "DS1-P", "DS1-V" and "DS1-A", respectively. The twist angle, twist angle velocity, and twist angle acceleration corresponding with the improved drive side plow are designated "DS2-P", "DS2-V" and "DS2-A", respectively. Again, the important observation in FIG. 32 is that the original drive side plow produced peak accelerations/decelerations that were much greater than those produced by the improved drive side plow.

As demonstrated in FIGS. 27 through 32, it is possible, therefore, to reduce the inertial loading effects acting upon the pad during the folding process by proper selection of the folding plow configuration. By doing so, a key factor contributing to skewing, fold-over and wrinkling of the pad during the folding process may be mitigated. In general, configuring the contoured surface so that twist angle increases approximately linearly (constant slope) reduces peak accelerations/decelerations that may lead to skewing, fold-over and wrinkling. However, the configuration of the improved, operator and drive side plows represented in FIGS. 27 through 32 is only one of numerous examples of configurations that minimize peak accelerations/decelerations of the wings and that may be adapted to the folding system to reduce skewing, fold-over and wrinkling.

Air Pressure System

Figure 33:
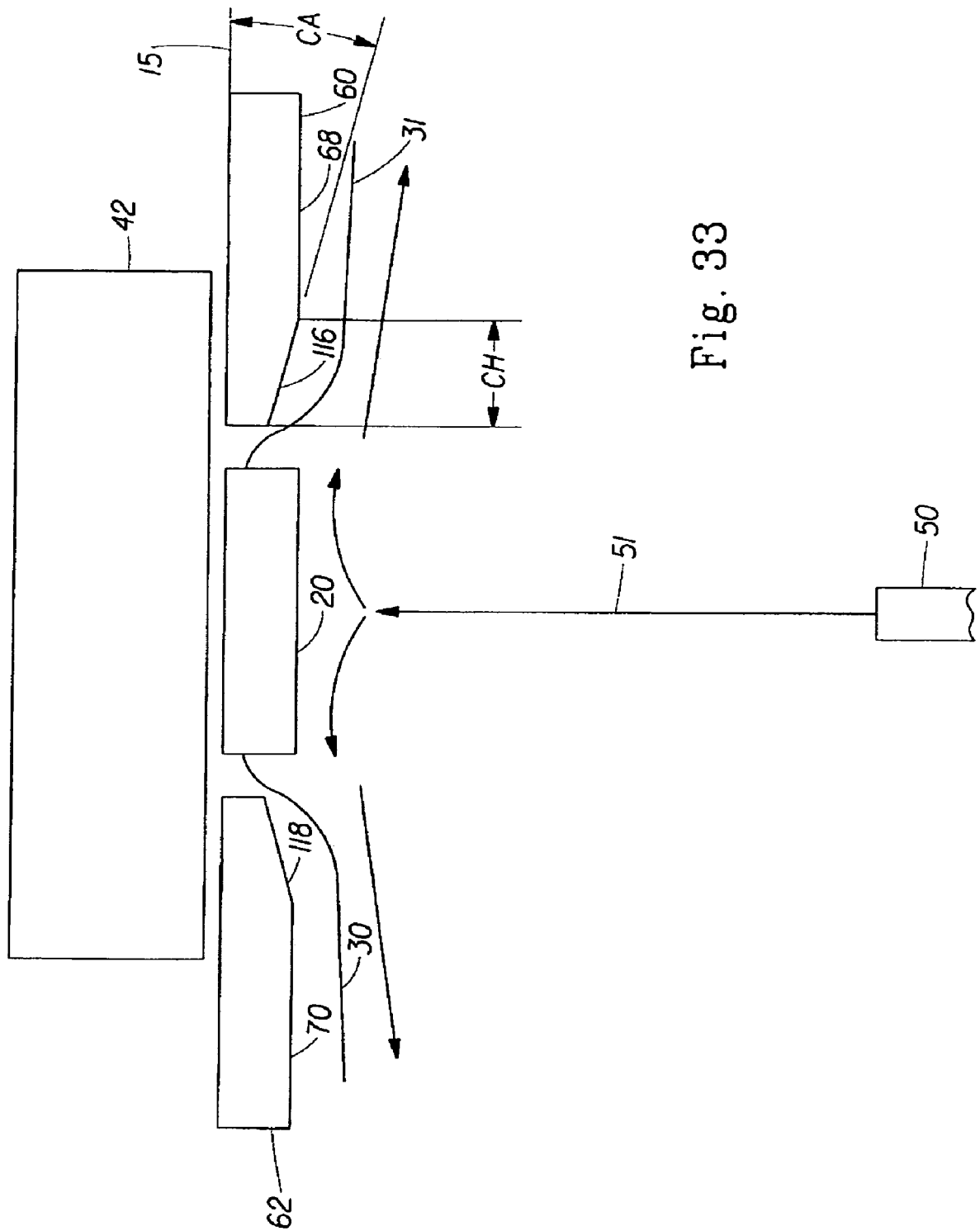
FIG. 33 is a cross-sectional view illustration of an air flow impinging upon a pad being conveyed along a pair of folding plows.

Referring again to folding system 10 shown in FIG. 1, and also to the illustration in FIG. 33, a plurality of blowers 50 may be positioned beneath third vacuum conveyor 42 to provide an air flow 51 (or "air fountain") that impinges upon the bottom of pad 20. Blowers 50 may be spaced apart and arranged approximately in a line beneath longitudinal web axis 22. Blowers 50 may be located near the exit end of second vacuum conveyor 34 such that air flow 51 provides an upward (against gravity) force on the conveyed pads 20 as they are transferred from second vacuum conveyor 34 to third vacuum conveyor 42 and slide along folding plows 44. (The vacuum provided by vacuum conveyor 42 holds central chassis 14, but allows wings 30, 31 to drop due to gravitational and aerodynamic effects.)

Although three blowers are shown in FIG. 1, there may be more or less than three blowers, which may be connected to a positive air pressure source (not shown). The blowers may be positioned beneath conveyor 42 in a plurality of arrangements. For example, blowers 50 may be spaced 50 millimeters apart and positioned about 200 millimeters beneath third vacuum conveyor 42. Many types of commercially available air nozzles are suitable for blowers 50, including air nozzles commonly referred to as "air knives". Air flow rate (meters$^3$/second) produced by blowers 50 may be adjusted according to various other parameters, including the distance between blowers 50 and conveyor 42, conveyor speed, stiffness of pad 20 materials, etc. Blowers 50 generate a higher than ambient air pressure beneath conveyor 42. A suitable pressure at a location beneath conveyor 42, for example, may be approximately in the range of 50-150 pascal.

Figure 34:
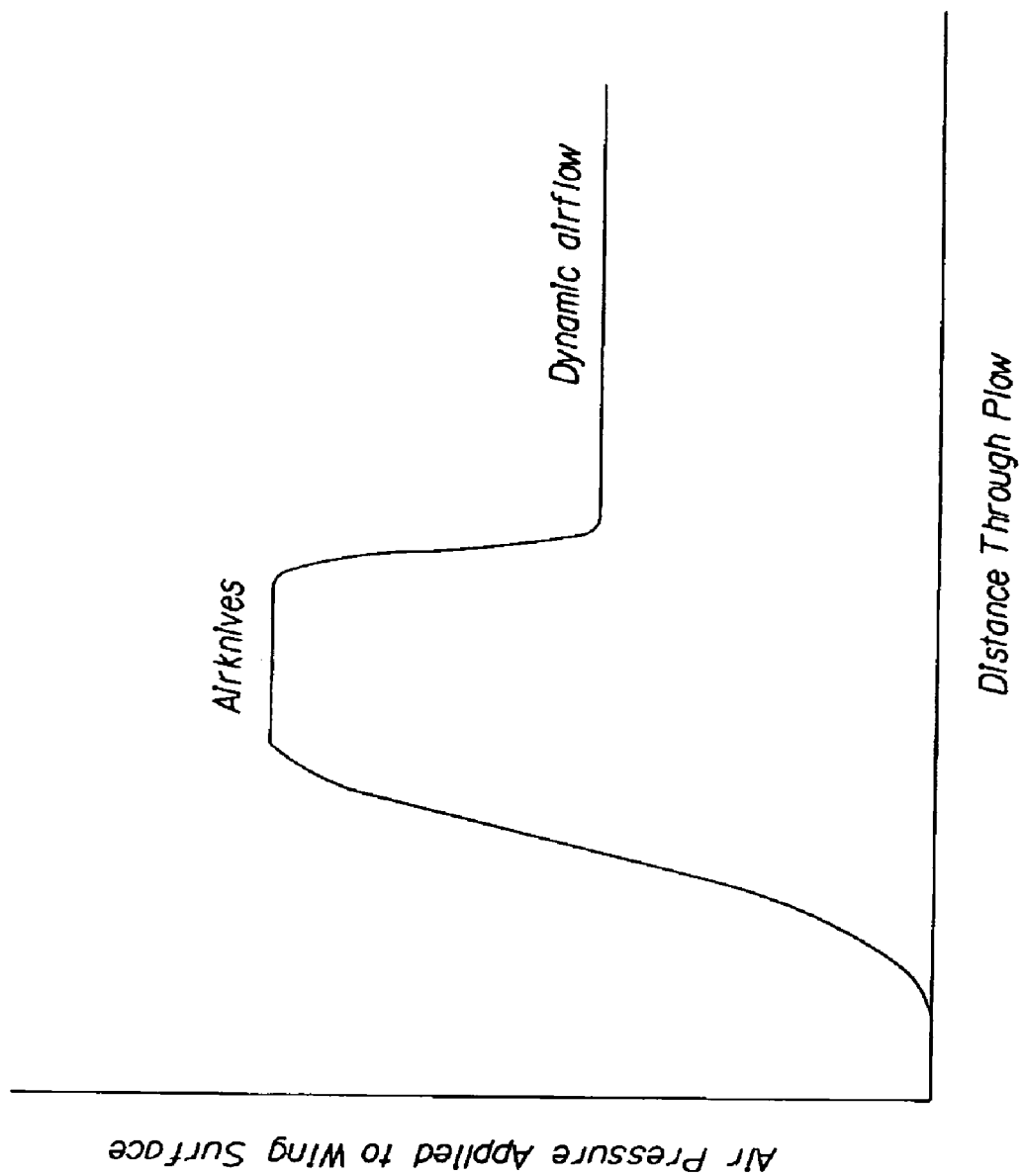
FIG. 34 is a graph depicting an air pressure profile.

Some portions of the folding system may require higher air flows than other portions to support pad 20. Therefore, a plurality of blowers 50 may also be provided to produce a plurality of air flows having different air flow rates in order to achieve a particular positive air pressure profile. FIG. 34 is a graph showing one example of a positive air pressure profile that may be used with folding system 10.

Blowers 50 may also produce a flow of a gas different than air or produce a flow of another gas mixed with air, to chemically and/or physically change a pad material property, temporarily or permanently, in order to improve the folding process, or otherwise improve the produced pads. For example, blowers 50 may produce a flow of an inert gas other than air to rapidly cool the pads in order to stiffen the pad materials so that wings 30, 31 may better resist aerodynamic and other types of loading effects.

Still referring to FIG. 33, drive side plow 60 may have an inside chamfer 116 adjacent to flat surface 68 near pad 20. Operator side plow 62 may have an inside chamfer 118 adjacent to flat surface 70 near pad 20. Inside chamfers 116, 118 are also shown in the perspective view of folding plows 44 in FIG. 7 and extend from inlet end 64 to contoured surfaces 68, 70, respectively. The inside chamfer may have, for example, a chamfer size "CH" approximately in the range of 5 to 25 millimeters and a chamfer angle "CA" approximately in the range of 10 to 60 degrees with respect to the central chassis plane 15. Inside chamfers 116, 118 allow a "more gradual" folding of wings 30, 31 than what is possible with non-chamfered plows, especially when used in combination with blowers 50, thereby helping to reduce wrinkling of wings 30, 31 (that may contribute to skewing and fold-over) prior to folding.

Figure 35:
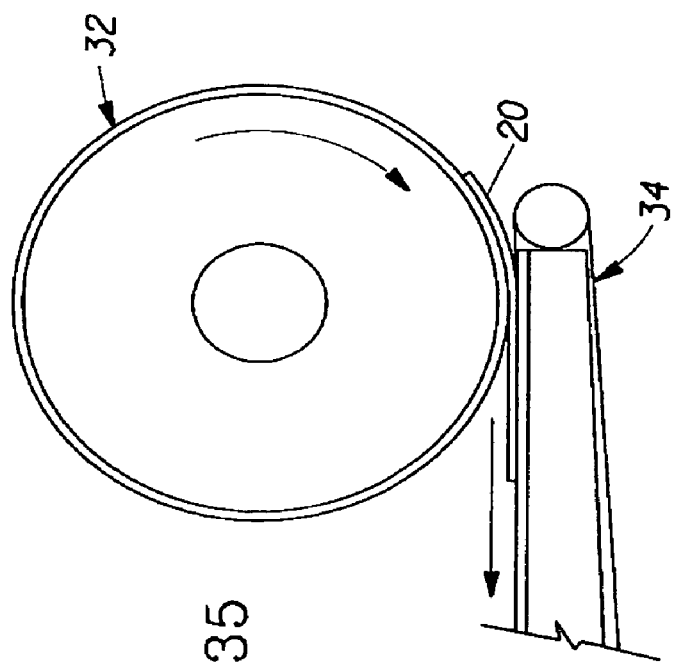
FIG. 35 is a operator side view of a transfer roll placing a pad onto a second vacuum conveyor.
Figure 36:
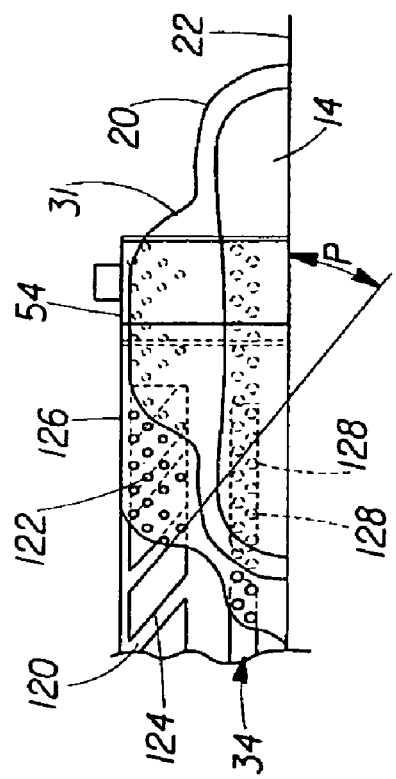
FIG. 36 is a partial top view of the second vacuum conveyor and the pad shown in FIG. 28.

FIG. 35 is an operator side view of a pad 20 coming off of transfer roll 32 and onto second vacuum conveyor 34. FIG. 36 is a partial top view of pad 20 held on second vacuum conveyor 34 (transfer roll 32 is removed for clarity). Conveyor 34 includes a moving belt 122 having a multiplicity of perforations 128. Conveyor 34 also includes a stationary back plate 120 having a plurality of spaced-apart slots 124 arranged in a row near an outer edge 126 of belt 122 so that wing 31 of pad 20 passes over slots 124. A mirror arrangement of space-apart slots may also be provided on the opposite side of back plate 120 and in the path of wing 30 of pad 20 (not shown). Slots 124 are in fluid communication with a vacuum source (not shown). As perforations 128 move over slots 124, vacuum may be communicated through perforations 128 to hold pad 20 on belt 122.

As shown in FIG. 36, each of slots 124 is angled with respect to longitudinal web axis 22 such that vacuum may be progressively communicated through perforations 128 to pad 20. Each slot may have an angle "P" that is approximately in the range of 30 to 60 degrees. As pad 20 passes over one of slots 124, vacuum initially communicates to the inward portion of wing 31, near central chassis 14. As pad 20 continues to pass over that one of slots 124, vacuum is progressively communicated towards outer edge 54 of wing 31. This progressive application of vacuum to wing 31 helps to prevent wrinkling of wing 31 as it is transferred from transfer roller 32 to conveyor 34, thereby improving pad transfer to the folding plows 44 and helping to prevent skewing and fold-over.

Rotary Knife

Another contributor to wrinkling during the pad manufacturing process is uneven "cross-web tensioning" that may occur during the cutting of individual pads from the moving web. As shown in FIG. 1, web 12 passes between a rotary knife 28 and a compression roller 29 so that individual pads are cut from web 12. As described earlier, the web 12 is formed form a plurality of relatively thick, pad cores 15 retained between thin top and backsheets, so that the wings of each pad 20 are much thinner than central chassis 14. Because of this thickness variation, the tension of the web material in the longitudinal direction may vary across the width of web 12 as it passes between compression roller 29 and rotary knife 28. This tension variation may lead to wrinkling of pad 20 as it is cut from the web 12, and the wrinkling may eventually contribute to wing-fold skew and/or fold-over.

FIG. 37 is an isometric view of rotary knife 28 (also shown in FIG. 1) for cutting individual pads from the continuous, moving web 12. FIG. 38 is a cross-sectional view taken at line 38-38 of rotary knife 28 in FIG. 37. Rotary knife 28 includes a cylindrical drum 134 having a drum surface 136 around a hub 132. At least one knife 130 having the shape of pad 20 may be attached to or formed on drum surface 136. A central chassis recess 142 includes a recess insert 140 with a insert surface 138. Central chassis recess 142 has a profile that is similar in shape but slightly greater in size than central chassis 14 of pad 20. Rotary knife 28 is phase driven on folding system 10 such that each central chassis 14 inserts into central chassis recess 142 as pad 20 is cut from the moving web. Central chassis recess 142 may have a depth that is smaller than the thickness of central chassis 14 of pad 20 so that central chassis 14 is compressed as the moving web 12 passes between rotary knife 28 and compression roller 29. Recess insert 140 may be removably attached to drum 134 in recess 142. A plurality of recess inserts of different thicknesses may be provided so that the desired compression may be applied to different thicknesses of pad cores (such as for different products). Providing rotary knife 28 with an adjustable depth recess 142 to accommodate central chassis thickness helps to equalize web tension in the longitudinal direction across the entire width of web 12 and prevent pad wrinkling, thereby lessening wing-fold skew and/or fold-over.

Bonding Roll Speed

Figure 39:
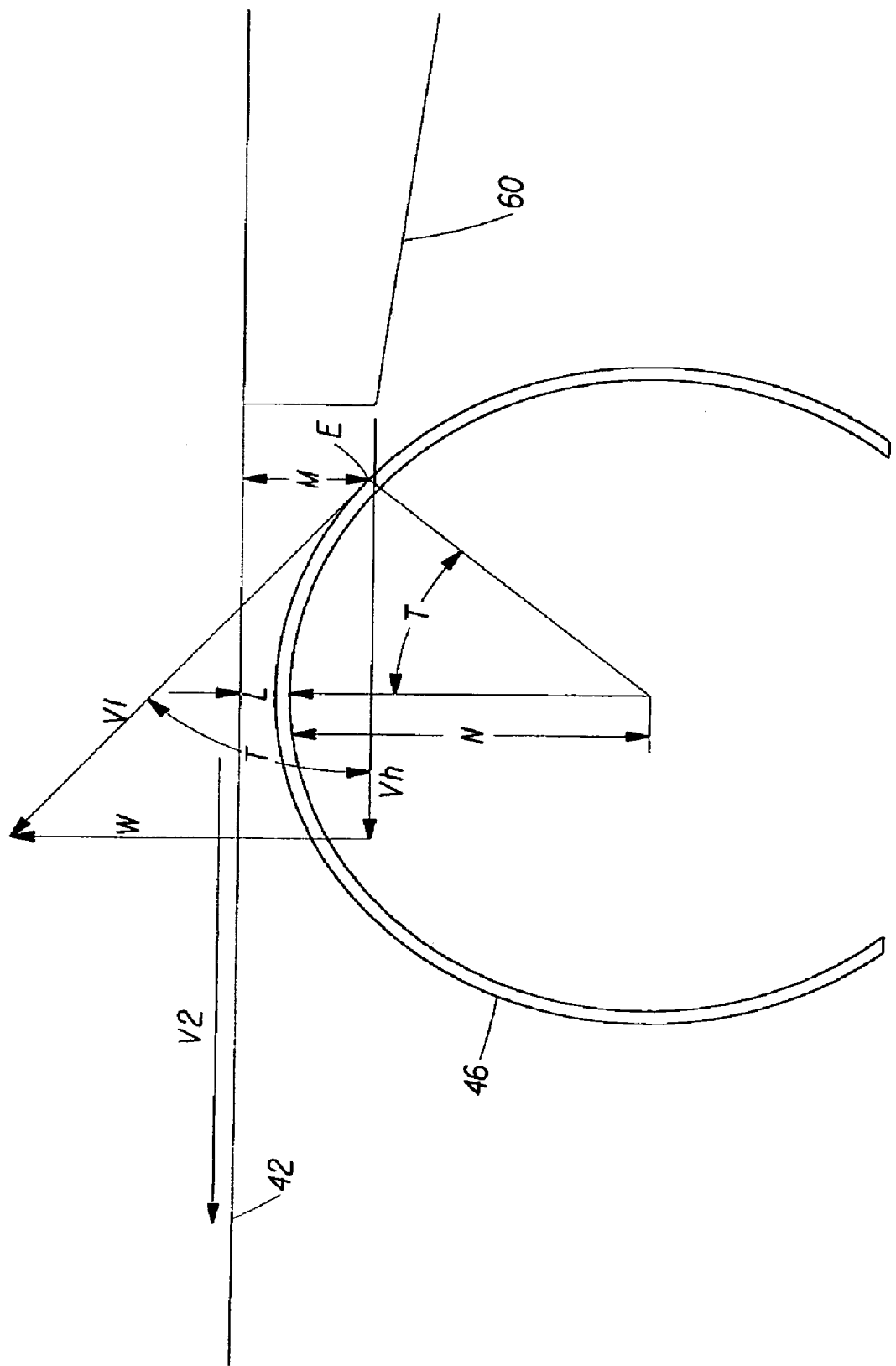
FIG. 39 is a diagram showing velocity vectors and geometrical parameters for a bonding roll and a third vacuum conveyor.

Referring yet again to FIG. 1, pad 20 exits from folding plows 44 and engages bonding roll 46 as described earlier. Skewing and fold-over has also been determined to occur during this step of the pad manufacturing process. FIG. 39 is a simplified diagram showing bonding roll 46 positioned near the exit end of drive side plow 60 and beneath third vacuum conveyor 42 by a distance "L". A pad (not shown) exits plow 60 and engages bonding roll 46 approximately at an engagement point "E", which is a distance "M" below conveyor 42. The tangential velocity "V1" of bonding roll 46 is directed at an angle "T" with respect to the conveyor velocity "V2". V1 may be resolved into a horizontal velocity component "Vh" and a vertical velocity component "Vv" as shown.

As described earlier, release tape 16 may initially be adhered to wing 31 of pad 20 and then folded around central chassis 14 by drive side plow 60. Prior to passage through bonding roll 46, release tape 16 may not yet be completely bonded to wing 30 on the operator side. Therefore, wing 31 with the extra mass of release tape 16 is highly susceptible to skewing when wing 31 and tape 16 impact bonding roll 46. It has been determined that this skewing may be reduced by "over-speeding" bonding roll 46, such that V1 is greater than V2, in order to lessen the difference between Vh and V2. For example, if M=18 mm, L=6 mm and N=50 mm, V1 may be approximately 7-15% higher than V2 to reduce skewing of wing 31. This percentage may vary according to the thickness of pad core 15. For example, V1 may be approximately 1.07 times greater than V2 for pads having relatively thin pad cores (for example, 3 to 5 millimeters thick), and V1 may be approximately 1.15 times greater than V2 for pads having relatively thick pad cores (for example, 15 to 18 millimeters thick).

Method for Analyzing the Operation of a Folding System

Computer aided engineering (CAE) tools and methods may be used to solve complex engineering problems via computer simulations. CAE includes the use of finite element analysis (FEA) software, computational fluid dynamics (CFD) software, mechanism software, optimization software and a host of other tools to simulate mechanical, chemical and numerous other types of processes. The amount of computing power needed for these tools is very great, but recent advances in computing technology have enabled their cost-effective application in industries that previously relied primarily on empirical analysis techniques.

In order for CAE tools and methods to be used for analyzing the operation of a folding system, the physics of the folding process may first be examined. The most relevant physical parameters and process conditions may be determined and inputted into a mathematical model that includes CFD codes to solve the Navier-Stokes equations, FEA codes to solve the equations of motion coupled with the material constitutive equations, and kinematics codes to numerically solve the equations of motion given movement constraints, contact requirements, and so on. Much of the geometry of interest may be derived from the computer aided design (CAD) models of the relevant components, including the folding plows.

Figure 40:
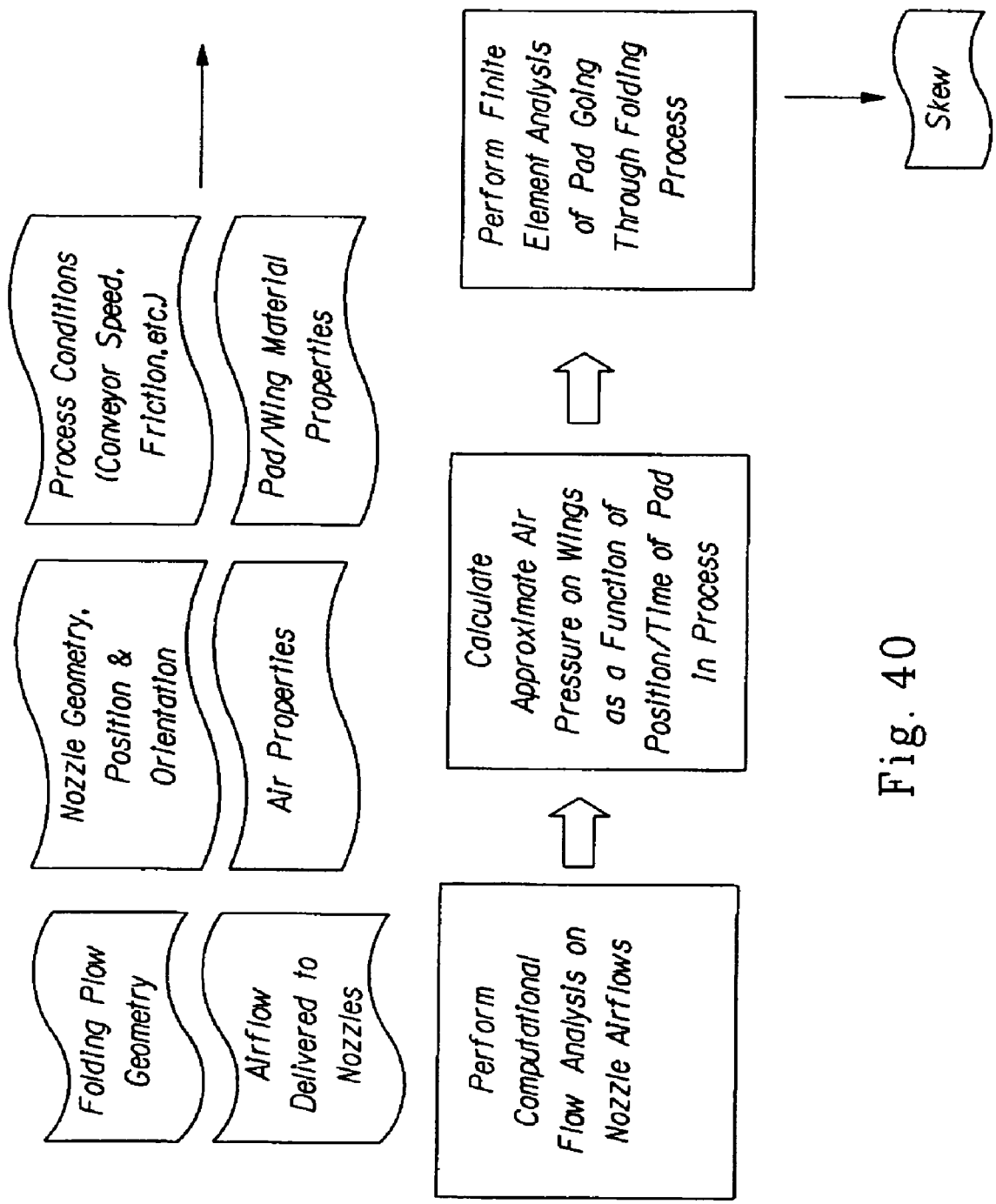
FIG. 40 is a flow chart describing a method for analyzing a folding system during operation.

FIG. 40 is a flowchart showing a method for analyzing the operation of a folding system such as shown in FIG. 1. The method incorporates the CFD, FEA, CAD and other tools, together with a strong understanding of the most relevant physics involved in the process, to provide a unique approach to predicting certain performance parameters such as the magnitude of skew of the folded wings of the pads. These software tools are well-known and commercially available. The resulting analysis provides direction for optimizing the design of the folding system and process.

FIG. 41 is a diagram of the most relevant components of the folding system and many of the required geometric input parameters.

An initial step of the method for analyzing the operation of a folding system is to provide a plurality of input parameters and properties that are relevant to the analysis. A plurality of folding plow geometrical parameters may be derived from the CAD, three-dimensional model, and may be based on the twist angle velocity/acceleration metrics shown in FIGS. 27 through 32, for example.

For the CFD analysis, a plurality of nozzle geometrical parameters may be provided, based on the design of blowers 50 (FIG. 1) for example, to determine the effective area that airflow passes through. The airflow delivered to the nozzles from the positive air pressure source may be provided to determine the volumetric flow rate (cubic meters/second, cubic feet/minute, etc.) of air passing through the nozzles to create the upward air flow. The position and orientation of each nozzle may be provided to simulate the generated airflows. A plurality of air properties may be provided, including the air density and viscosity. Temperature effects on the air properties may also be provided in the analysis.

For the FEA analysis, a plurality of pad/wing material properties may be provided. Many of these pad/wing material properties may be derived from actual stress/strain testing on various areas of interest of the pad, such as near folding lines and areas where wrinkling is likely to occur. The results of the test may be used to calculate the intrinsic properties of the various pad material components. The properties may then be incorporated into a constitutive material model such as is well-known in the art. A plurality of process conditions may also be provided, including the linear velocity of the pad, and the static and kinetic coefficient of friction between the pad surfaces and the folding plows. Other process conditions that may be provided pertain to the process set-up and the position of the pad on the conveyors, as shown in FIG. 41.

As shown in FIG. 40, the method includes performing the computational flow analysis on the nozzle airflows and calculating the approximate air pressure distribution on the wing surfaces as a function of pad position and time during the folding process. The method also includes performing the finite element analysis of the pad going through the folding process. Although the wing-folding process may be treated as a fluid-structures interaction (FSI) system (in which airflow affects the shape of the structure and the shape of the structure affects the airflow), FEA provides a sufficiently good analysis of structural deformations during the process.

The method of analyzing the folding system during operation may provide a prediction of a plurality of performance parameters, including wing-folding skew as defined previously. For example, the method may provide a FEA picture of a folded pad such as shown in FIG. 2, and also including the finite element mesh used in the analysis. Once the mathematical model is created and validated by tests, various input parameters, properties and conditions may be easily changed and the automated analysis repeated to view the effects of the changes. In this way it is possible to optimize the design of components such as the folding plows and to select desirable process conditions such as air flow volume and conveyor speed.

Although an improved folding system and process, and a method of analyzing the operation of a folding system has been shown and described with respect to certain aspects, variations, and embodiments, it should be understood that modifications may occur to those skilled in the art. For example, the improved folding system and process described herein, and the method of analyzing a folding system during operation, are equally applicable to other types of absorbent articles having folds, including baby and adult diapers, facial tissues, wipes and other implements.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A folding system for folding at least one flap extending from a central chassis of each of a plurality of absorbent articles formed from a continuous moving web moving in a longitudinal direction, the folding system comprising:
   a flap-folding conveyor that holds the central chassis of each absorbent article and moves each absorbent article in the longitudinal direction;
   at least one elongated, folding plow mounted alongside the flap-folding conveyor and including:
      an entrance end, an exit end and an inner edge that define a twist axis that is parallel to the longitudinal direction; and
      a contoured surface having a configuration defined by a twist angle that increases along the twist axis from zero degrees near the entrance end to 180 degrees near the exit end, wherein the twist angle is formed by the intersection between a first plane containing the central chassis and a second plane containing the contoured surface and may be measured in a twist angle plane section transverse to the twist axis for any location along the twist axis, wherein said folding plow has a transition corner intersecting an inner edge and outer edge of said folding plow, wherein said transition corner has an inner transition point and an outer transition point, wherein said inner transition point and said outer transition point have an angular offset in the longitudinal direction, wherein the twist angle plane section is oriented at an angle with respect to the twist angle axis, thereby forming an angular offset distance such that the portion of the flap near the central chassis begins to fold prior to the remaining portion of the flap;
   wherein the flap-folding conveyor moves the central chassis along the inner edge of the folding plow and the flap slides against the contoured surface from the entrance end to the exit end, such that the flap folds around the central chassis near the inner edge.

2. The folding system of claim 1, wherein the twist angle increases approximately linearly along the twist axis.

3. The folding system of claim 1, wherein the twist angle plane section is oriented at an angle approximately in the range of 30 to 60 degrees with respect to the twist angle axis.

4. The folding system of claim 1, wherein the folding plows further include an elongated, flat surface positioned near the entrance end and in-line with the contoured surface such that the flap-folding conveyor moves the absorbent article as the flap slides along the flat surface before the flap engages the contoured surface, and wherein the flat surface includes a chamfered inner edge that transitions into the inner edge of the contoured surface.

5. The folding system of claim 4, wherein the chamfered inner edge has a chamfer size approximately in the range of 5 to 25 millimeters and a chamfer angle approximately in the range of 10 to 60 degrees with respect to the first plane containing the central chassis.

6. The folding system of claim 1, wherein the folding plow further includes a throat region near the exit end and having an inner corner, wherein the radius of the inner corner is approximately in the range of 2 to 10 millimeters.

7. The folding system of claim 1, further comprising at least one blower positioned near the flap-folding conveyor and generating a gas flow impinging upon the absorbent article, thereby helping to hold the flap against the folding plow.

8. The folding system of claim 7, further comprising a plurality of blowers positioned near the conveyor and generating a positive pressure profile impinging upon the absorbent article, thereby helping to hold the flap against the folding plow.

9. The folding system of claim 7, wherein the gas flow is primarily composed of air.

10. The folding system of claim 7, further comprising:
    a transfer conveyor for moving each absorbent article to the flap-folding conveyor, the transfer conveyor including:
       a moving belt having a multiplicity of perforations;
       a stationary back plate supporting the moving belt and in fluid communication with a vacuum source, the back plate having a plurality of spaced-apart slots arranged in a row near an outer edge of the moving belt such that the perforations of the moving belt and the flap of each absorbent article passes over the slots, wherein each slot is oriented at a slot angle with respect to the longitudinal direction; and
    a transfer roll for moving each absorbent article from the continuous moving web to the transfer conveyor;
    whereby vacuum is progressively communicated through the slots and the perforations to the flap in an outwardly direction from the central chassis, thereby smoothing the transfer of each pad from the transfer roll to the transfer conveyor.

11. The folding system of claim 10, wherein the slot angle is approximately in the range of 30 to 60 degrees.

12. The folding system of claim 10, further comprising a slip-and-cut device positioned near the transfer conveyor, wherein the slip-and-cut device forms a release tape with an adhesive applied thereto for each absorbent article and attaches the release tape to the flap of the absorbent article as the absorbent article is moved by the transfer conveyor.

13. The folding system of claim 1, further comprising:
    a cylindrical, phase-driven, rotary knife having a drum surface disposed around a hub, the rotary knife including:
       at least one knife having the shape of the absorbent article and positioned on the drum surface; and
       a recess in the drum surface positioned within an area defined by each knife; and
    a compression roller in rolling engagement with the rotary knife;
    wherein the continuous moving web passes between the rotary knife and the compression roller such that the central chassis of each absorbent article locates into the recess as the knife cuts each absorbent article from the moving web, thereby equalizing the tension in the longitudinal direction of the moving web across the width of the moving web near the rotary knife.

14. The folding system of claim 13, wherein the rotary knife further includes a recess insert that removably attaches to the inside of the recess, such that the depth of the recess may be adjustable.

15. The folding system of claim 1, further comprising a bonding roll positioned near the exit end of the folding plow and near the flap-folding conveyor such that each absorbent article moves off of the folding plow and is compressed within a gap between the flap-folding conveyor and the bonding roll, wherein the flap-folding conveyor is driven at a conveying velocity in the longitudinal direction, and wherein the bonding roll is rotatably driven such that a tangential velocity of the bonding roll is in approximately the same direction as the conveying velocity near the gap, and the tangential velocity is greater than the conveying velocity.

16. The folding system of claim 15, wherein the tangential velocity of the bonding roll is approximately 7 to 15% greater than the conveying velocity of the flap-folding conveyor.

17. The folding system of claim 1 for folding a first flap and a second flap extending from opposite sides of the central chassis, wherein the folding system includes an operator side folding plow spaced apart from a driver side folding plow, such that the first flap slides on the operator side folding plow and the second flap slides on the driver side folding plow, and the first and second flaps fold around the central chassis.

* * * * *